United States Patent [19]

Yamada et al.

[11] Patent Number: 5,235,510
[45] Date of Patent: Aug. 10, 1993

[54] COMPUTER-AIDED DIAGNOSIS SYSTEM FOR MEDICAL USE

[75] Inventors: Shinichi Yamada; Kenichi Komatsu; Takehiro Ema, all of Tochigi, Japan

[73] Assignee: Kabushiki Kaisha Toshiba, Kawasaki, Japan

[21] Appl. No.: 796,579

[22] Filed: Nov. 22, 1991

[30] Foreign Application Priority Data

Nov. 22, 1990 [JP] Japan ................................. 2-320498

[51] Int. Cl.⁵ ............................................. G06F 15/00
[52] U.S. Cl. ........................... 364/413.02; 364/413.22; 364/413.20
[58] Field of Search ...................... 364/413.02, 413.22, 364/413.20

[56] References Cited

U.S. PATENT DOCUMENTS

| | | | |
|---|---|---|---|
| 4,839,807 | 6/1989 | Doi et al. | 364/413.13 |
| 4,841,555 | 6/1989 | Doi et al. | 378/99 |
| 4,851,984 | 7/1989 | Doi et al. | 364/413.23 |
| 4,875,165 | 10/1989 | Fencil et al. | 364/413.22 |
| 4,907,156 | 3/1990 | Doi et al. | 364/413.13 |
| 4,918,534 | 4/1990 | Lam et al. | 358/225 |
| 5,005,126 | 4/1992 | Haskin | 364/413.22 |
| 5,072,384 | 12/1991 | Doi et al. | 364/413.13 |
| 5,086,392 | 2/1992 | Nakajima | 364/413.22 |

Primary Examiner—Roy N. Envall, Jr.
Assistant Examiner—Ari M. Bai
Attorney, Agent, or Firm—Oblon, Spivak, McClelland, Maier & Neustadt

[57] ABSTRACT

A picture archiving communication system for storing, transferring various digital image data in a single or a plurality of hospitals includes a modality, a data base, a workstation as a display unit, and a network for connecting these components. The modality includes various diagnosis apparatuses for generating medical digital images, such as a film digitizer, an angiography apparatus, a CT scanner, an MRI system, a nuclear medicine diagnosis apparatus, an ultrasound diagnosis apparatus, and an electric endoscope. An examination ordering system is connected to the network. The workstation outputs computer-aided diagnosis data obtained by analyzing medical image data by means of a computer. This computer-aided diagnosis data includes the location, the type, and the degree of abnormality. In order to alarm an abnormality, the workstation displays a marker pointing the portion of the abnormal portion on the image, a text sentence representing the details of the abnormality. The computer-aided diagnosis data is obtained before its output is requested. The computer-aided diagnosis data is stored in a semiconductor memory until its output is requested.

57 Claims, 33 Drawing Sheets

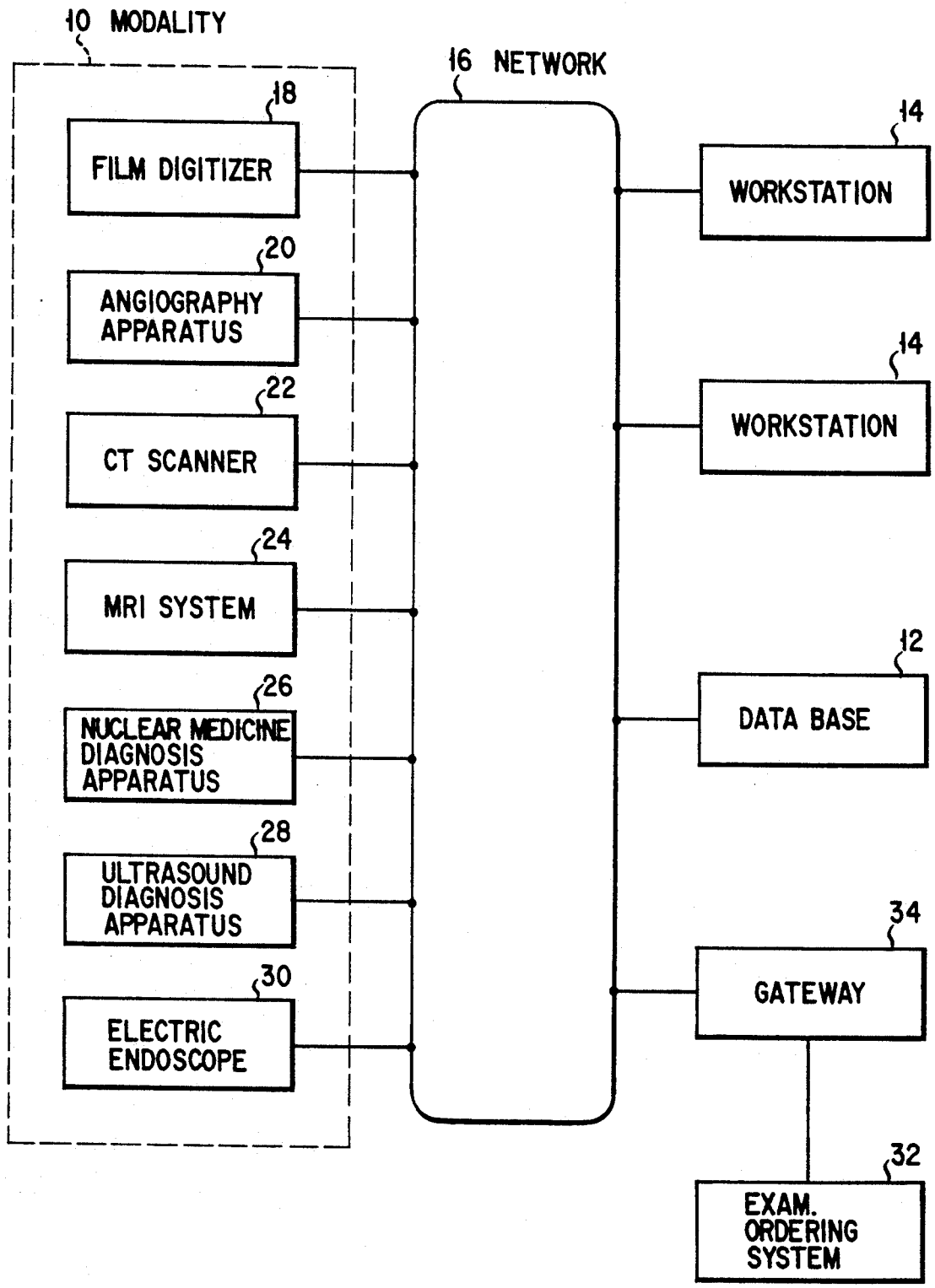
F I G. 1

| EXAMINATION DATA |
| --- |
| EXAM. ID NUMBER |
| PATIENT ID NUMBER |
| NAME OF PATIENT |
| BIRTHDAY |
| SEX DISTINCTION |
| MODALITY |
| OBJECT |
| DATE |
| EXAM. REQUESTING DEPARTMENT |
| NAME OF DOCTOR |
| THE NUMBER OF IMAGES |
| ⋮ |

FIG. 2

| EXAM. DATA (X-RAY RADIOGRAPH OF CHEST) ||
|---|---|
| EXAM. ID | K3-905-002-005 |
| PATIENT ID | N-T-239650 |
| NAME | · · · · · · |
| BIRTHDAY | '55-4-5 |
| SEX | MALE |
| MODALITY | CONVENTIONAL RADIOGRAPH |
| OBJECT | CHEST |
| DATE | '90-3-3 |
| DEPARTMENT | SURGERY |
| DOCTOR | · · · · · · |
| THE NUMBER OF IMAGES | 4 |

FIG. 3

| RELEVANT DATA |
|---|
| EXAM. ID |
| IMAGE ID |
| SIZE OF IMAGE (WIDTH) |
| SIZE OF IMAGE (LENGTH) |
| MATRIX SIZE (WIDTH) |
| MATRIX SIZE (LENGTH) |
| BIT LENGTH OF PIXEL DATA |
| AMOUNT OF IMAGE DATA |
| RESULT OF CAD<br>ID1<br>ADDRESS 1 |
| RESULT OF CAD<br>ID2<br>ADDRESS 2 |
| ⋮ |
| RESULT OF CAD<br>IDn<br>ADDRESS n |
| THE NUMBER OF APPLICATIONS OF CAD ALGORITHM |
| IMAGING DIRECTION |
| READING |

F I G. 5

| RELEVANT DATA ||
|---|---|
| EXAM. ID | K3-905-002-005 |
| IMAGE ID | 2 |
| SIZE OF IMAGE (WIDTH) | 500 |
| SIZE OF IMAGE (LENGTH) | 500 |
| MATRIX SIZE (WIDTH) | 1024 |
| MATRIX SIZE (LENGTH) | 1024 |
| BIT LENGTH OF PIXEL DATA | 10 |
| AMOUNT OF IMAGE DATA (MB) | 5 |
| RESULT OF CAD ID1 ADDRESS 1 | A1111 |
| RESULT OF CAD ID2 ADDRESS 2 | NOTHING |
| ⋮ | ⋮ |
| RESULT OF CAD IDn ADDRESS n | NOTHING |
| THE NUMBER OF APPLICATIONS OF CAD ALGORITHM | 0 |
| IMAGING DIRECTION | FRONT |
| READING | NOTHING |

FIG. 6

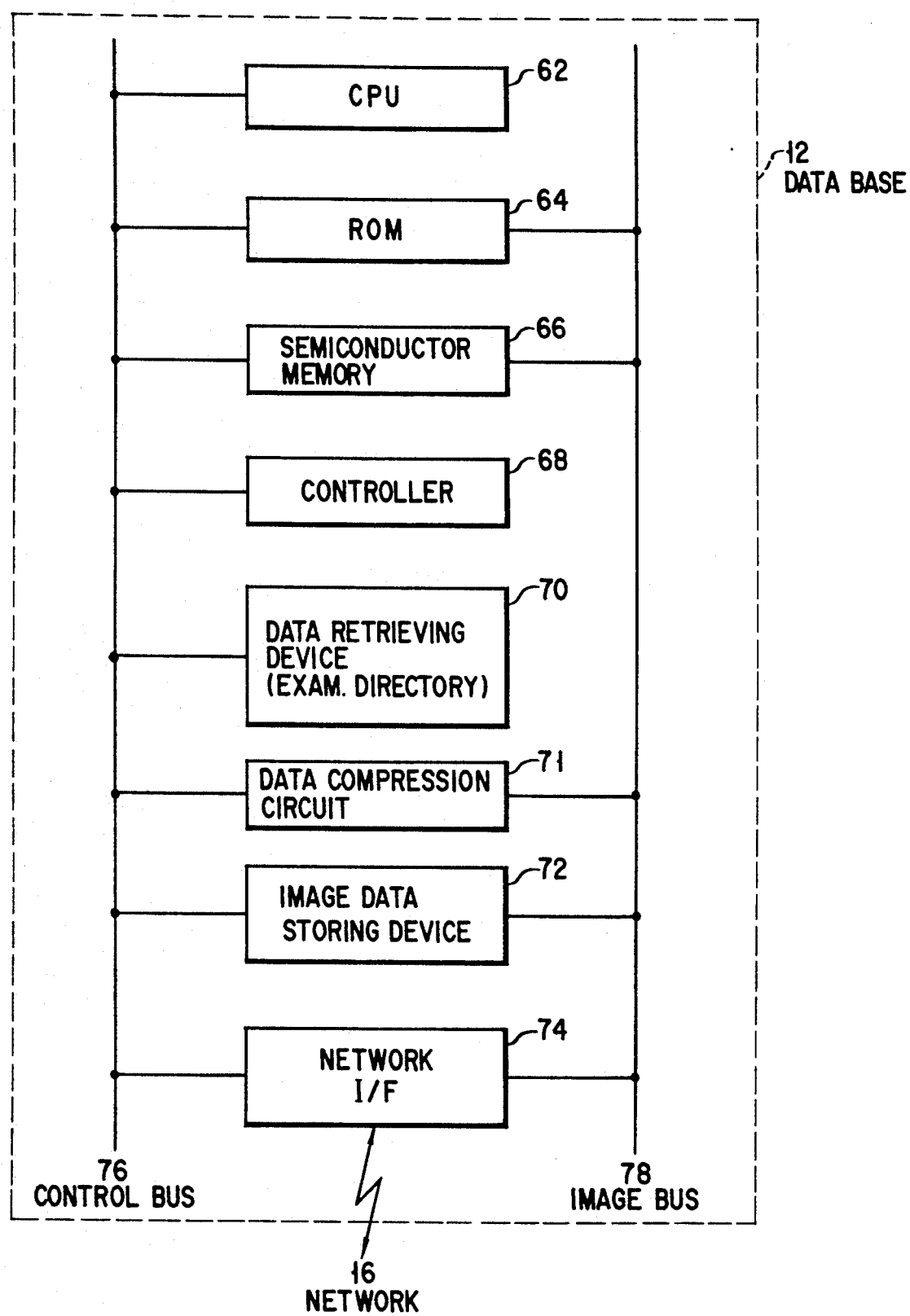
F I G. 8

| EXAM. DIRECTORY |
|---|
| EXAM. ID |
| PATIENT ID |
| NAME OF PATIENT |
| BIRTHDAY |
| SEX |
| MODALITY |
| EXAM. OBJECT |
| EXAM. DATE |
| EXAM. DEPARTMENT |
| EXAM. REQUESTING DOCTOR |
| THE NUMBER OF IMAGES |
| ⋮ |
| ADDRESS OF READING REPORT |
| AMOUNT OF RERORT DATA |
| ADDRESS OF RELEVANT DATA |
| AMOUNT OF RELEVANT DATA |
| ADDRESS OF IMAGE DATA |
| AMOUNT OF IMAGE DATA |
| RESULT OF CAD ID1 ADDRESS 1 |
| ⋮ |
| RESULT OF CAD IDn ADDRESS n |
| ⋮ |
| ADDRESS OF RELEVANT DATA |
| AMOUNT OF RELEVANT DATA |
| ADDRESS OF IMAGE DATA |
| AMOUNT OF IMAGE DATA |
| RESULT OF CAD ID1 ADDRESS 1 |
| ⋮ |

- EXAM. DATA: rows from EXAM. ID through AMOUNT OF RERORT DATA
- FIRST IMAGE: rows from ADDRESS OF RELEVANT DATA through RESULT OF CAD IDn ADDRESS n
- N-th IMAGE: final block

F I G. 9

| DOCTOR ID | REQUESTING DOCTOR ID | MODALITY | OBJECT | EXAM. ID |
|---|---|---|---|---|
| A3332 | B4441 | RADIOGRAPH | CHEST | C6661<br>C6662<br>. |
| A3333<br>.<br>.<br>. | | | | |

FRONT    SIDE    FRONT    SIDE

NON – READ    PAST (READ)

| CRT IMAGE DISPLAY CONTROL TABLE | | |
|---|---|---|
| CRT ID | EXAM. ID | IMAGE ID |
| 1 | K3-905-002-005 | 1 |
| 2 | K3-905-002-005 | 2 |
| 3 | | |
| 4 | | |
| ⋮ | ⋮ | ⋮ |

| NAME OF CAD ALGORITH | ATTRIBUTE DATA | |
|---|---|---|
| | ITEM | CONTENTS |
| INTERSTITIAL LUNG DISEASE | MODALITY | CONVENTIONAL RADIOGRAPH |
| | EXAM. OBJECT | CHEST |
| | IMAGING DIRECTION | FRONT |
| | RESULT OF CAD | NOTHING |
| MICRO CARCIFICATION DETECTION IN MAMMOGRAPHY | MODALITY | MAMMOGRAPH |
| | EXAM. OBJECT | MAMMA |
| | IMAGING DIRECTION | LEFT SIDE |
| | RESULT OF CAD | NOTHING |
| ⋮ | ⋮ | |
| HEART SIZE | MODALITY | CONVENTIONAL RADIOGRAPH |
| | EXAM. OBJECT | CHEST |
| | IMAGING DIRECTION | FRONT |
| | RESULT OF CAD | NOTHING |

FIG. 15

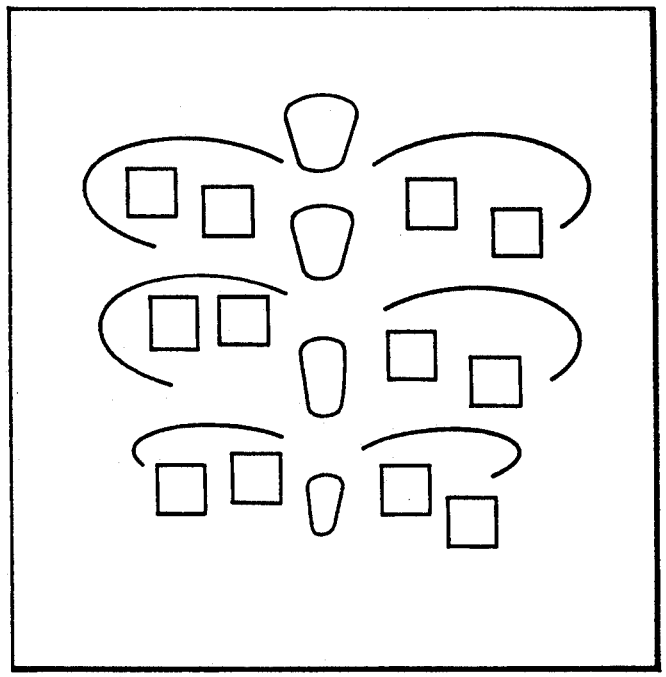
F I G. 16

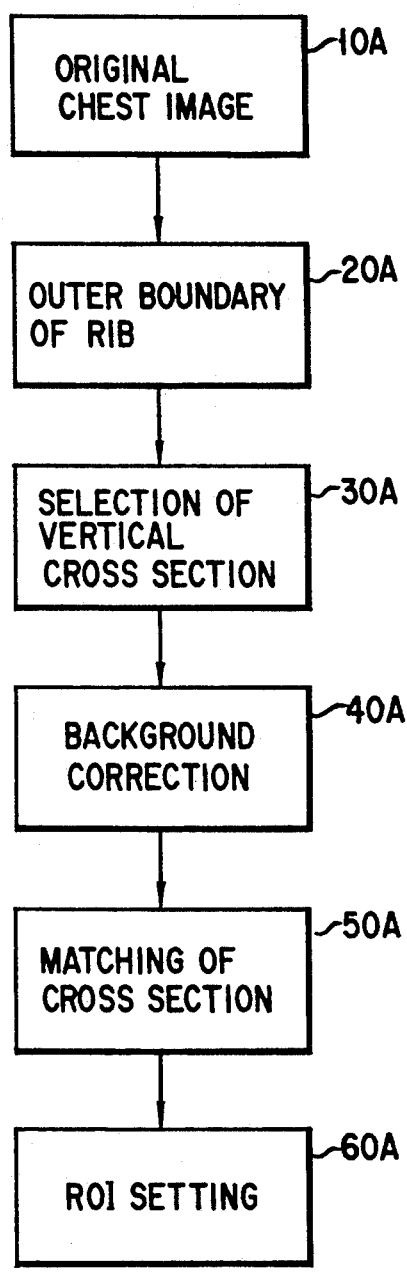
F I G. 17

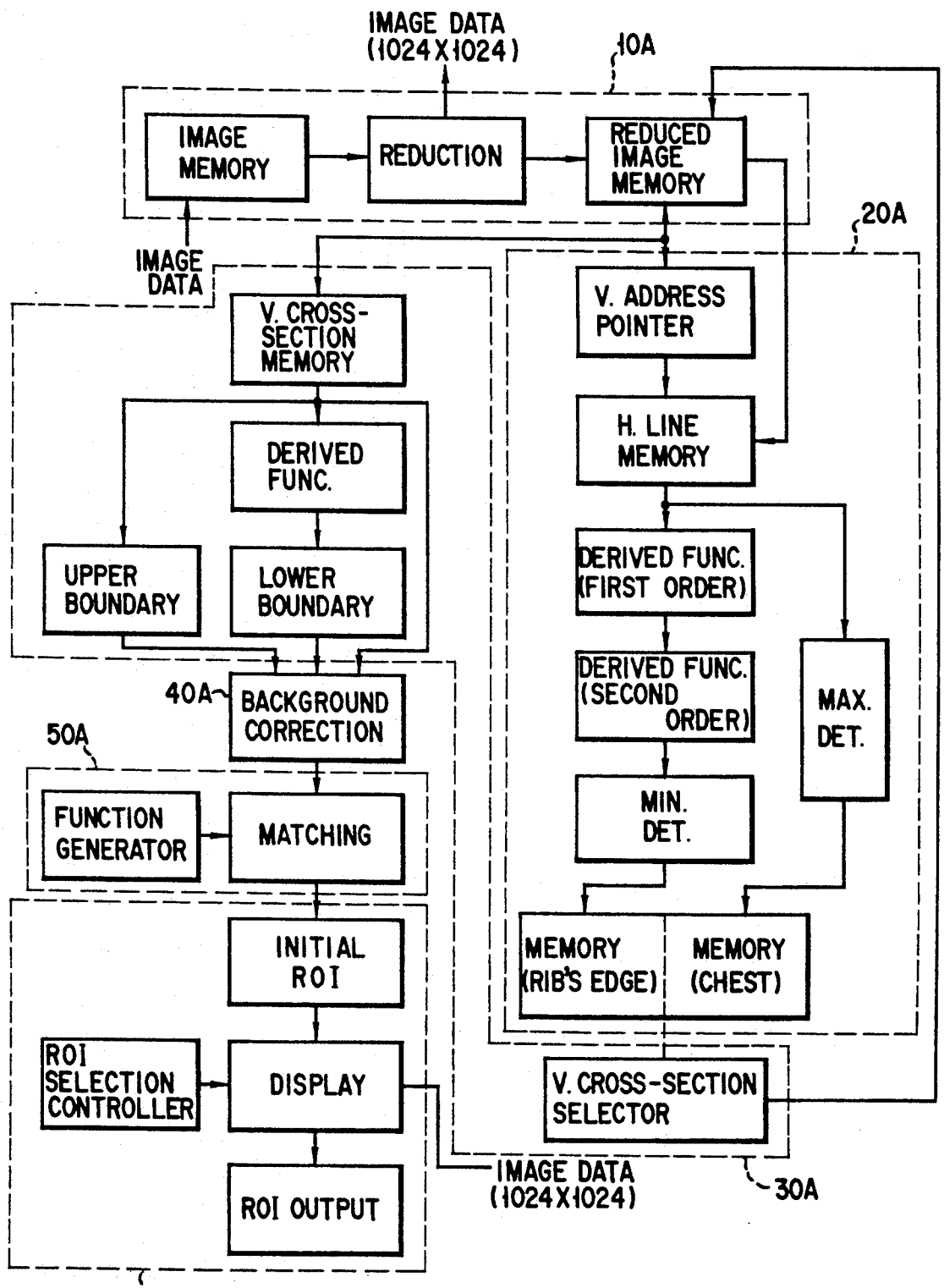
F I G. 18

FIG. 28

| EXPRESSION OF ABNORMALITY | | | | CONDITION OF THE NUMBER OF ABNORMAL ROIS |
|---|---|---|---|---|
| ABNORMAL | | | | MORE THAN TWO IN RIGHT, LEFT, UPPER, MIDDLE, OR LOWER |
| LUNG ABNORMAL | RIGHT | | | MORE THAN TWO IN RIGHT OR LEFT |
| | LEFT | | | |
| | UPPER | | | MORE THAN TWO IN UPPER OR LOWER |
| | MIDDLE | | | |
| | LOWER | | | |
| | RIGHT | UPPER | UPPER RIGHT | |
| | | MIDDLE | MIDDLE RIGHT | |
| | | LOWER | LOWER RIGHT | |
| | LEFT | UPPER | UPPER LEFT | |
| | | MIDDLE | MIDDLE LEFT | |
| | | LOWER | LOWER LEFT | |

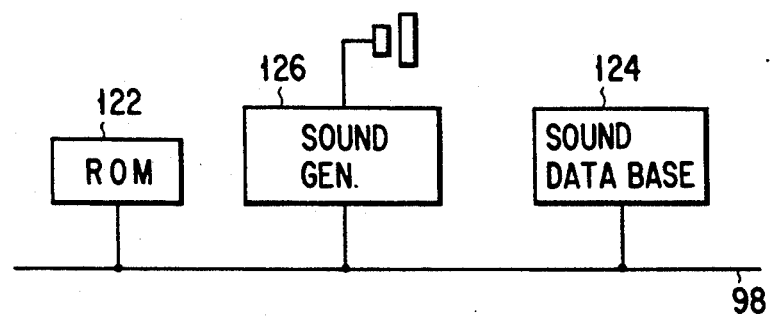
FIG. 37
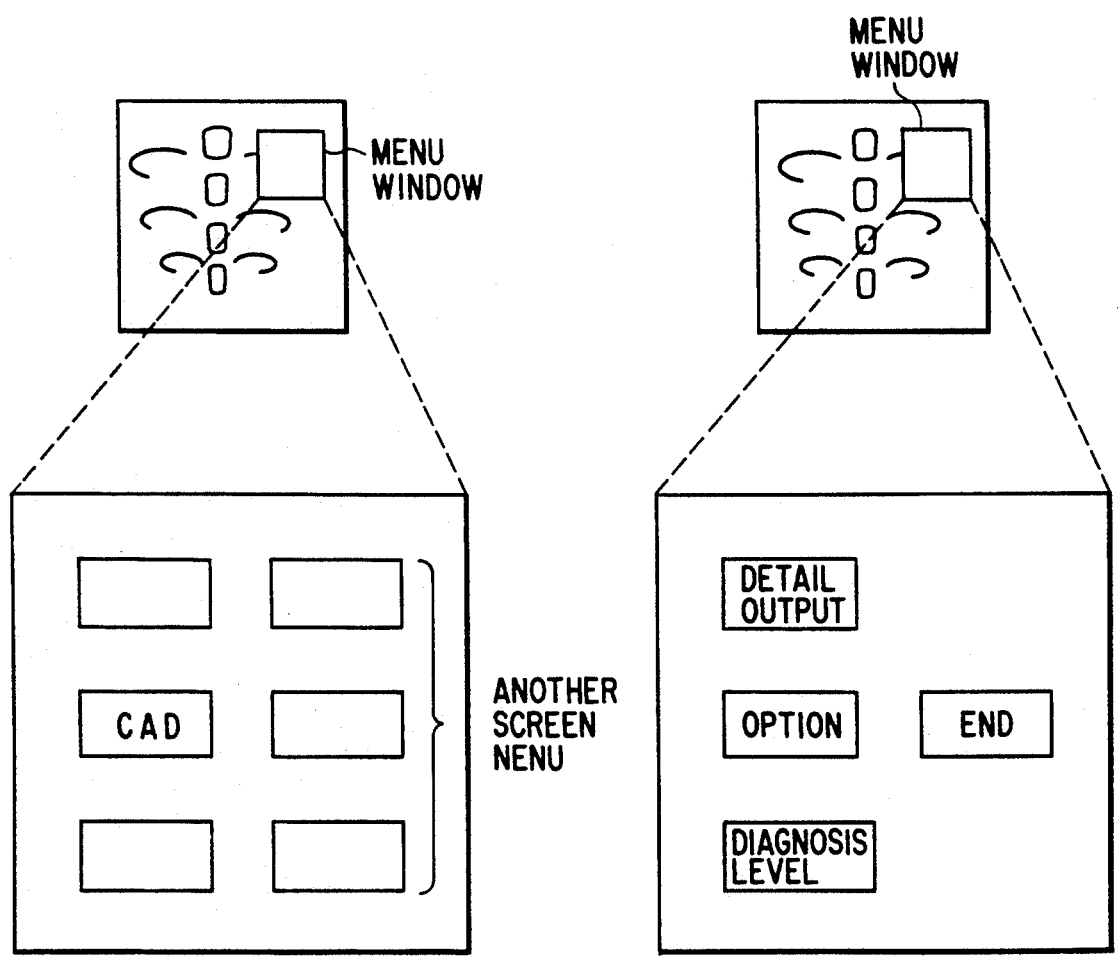
FIG. 38A
FIG. 38B

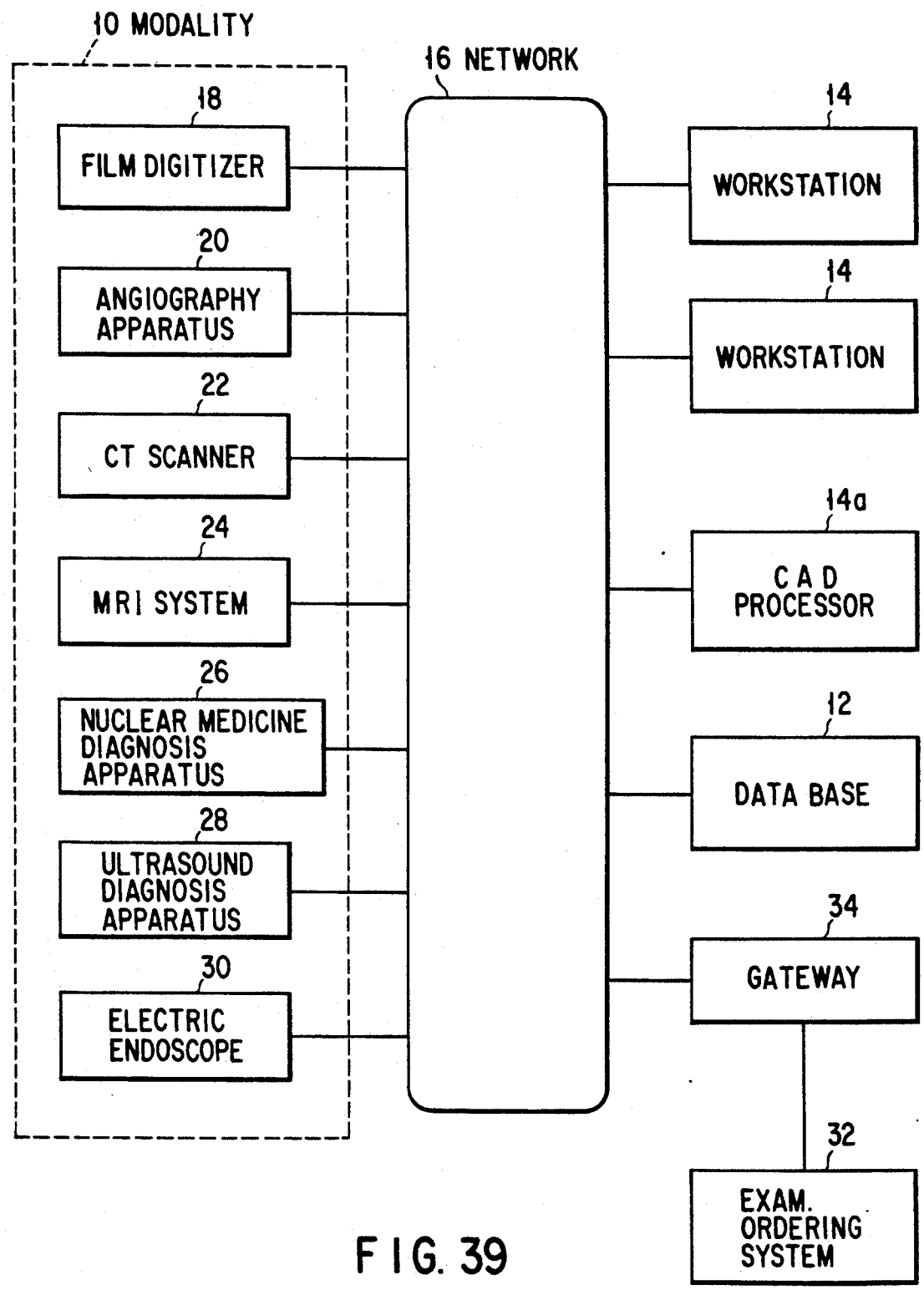
F I G. 39

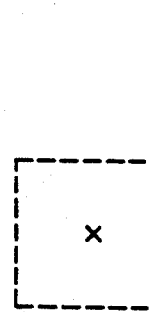 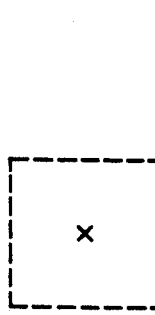 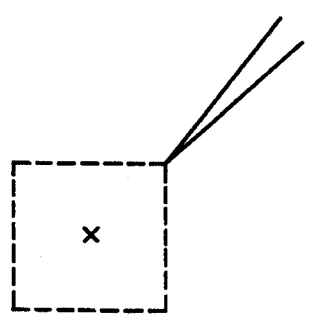
F I G. 40A   F I G. 40B   F I G. 40C
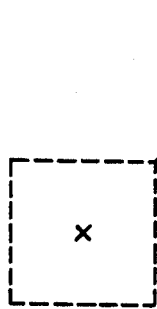 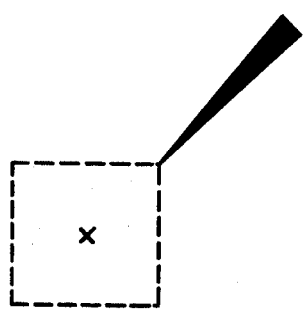
F I G. 40D   F I G. 40E

| INTERSTITIAL LUNG DISEASE DETECTION CAD |
|---|
| LUNG NODULAR SHADOW DETECTION CAD |
| . . . |
| HEAT SIZE DETECTION CAD |

F I G. 43

COMPUTER-AIDED DIAGNOSIS SYSTEM FOR MEDICAL USE

BACKGROUND OF THE INVENTION

1. Field of the Invention

The present invention relates to a computer-aided diagnosis system for medical use, which outputs computer-aided diagnosis data for medical images using a computer.

2. Description of the Related Art

Recently, a computer-aided diagnosis system (hereinafter referred to as a CAD system) for medical use has been developed in which the features of medical image data are determined and computer-aided diagnosis data (hereinafter referred to as CAD data) for assisting a doctor are obtained by using a computer. It is, however, cumbersome for a doctor to operate a computer to obtain the CAD data during the diagnosis, resulting in an adverse effect on a reading operation of image in terms of both time and labor. Further, the conventional CAD system itself cannot provide a high precision CAD data required for the diagnosis.

Examples of such CAD systems are disclosed in U.S. Pat. No. 4,851,984 and U.S. Pat. No. 4,839,807. The CAD systems described in the above USPs comprise means for inputting a medical image, means for analyzing the medical image using a predetermined CAD algorithm, and means for displaying an analysis result.

The doctor refers to the output of the CAD system at the time of reading of the medical image to prevent an oversight of a shadow image of the abnormal portion.

To obtain the CAD data, the following proceedings are required. Locations of one type of abnormal shadow images, e.g., an abnormal shadow image of the interstitial lung disease, are detected on a conventional X-ray radiograph and the result of the detection is output. Therefore, the medical image on the X-ray film is digitized. A rib, an object of the analysis, is identified in the medical image. A region of interest (hereinafter referred to as a ROI) is set on the medical image, as described in the U.S. Pat. No. 4,851,984. The data in the ROI is frequency-analyzed to extract the amount of physical texture of the image. The shadow image is classified into groups based on the amount of physical texture. A display device displays the digital image and the type, degree, and position of the shadow image in an overlapping manner.

The reading operation by the doctor is to draft the reading report. Before drafting the report, the doctor refers to the CAD data to prevent an oversight of a shadow image.

If the doctor needs the CAD data, the above proceedings must be performed. That is, the medical image must be digitized before the CAD system starts to operate. The digitized image is analyzed by the computer using the above proceedings and the analysis result is output to an attached display device. The doctor continues the reading of the image after watching the CAD result.

The above described CAD system has the following drawbacks.

The same CAD algorithm which is included in the CAD system is applied to the image data regardless of the type of the image. For example, the same CAD algorithm is applied to a conventional X-ray radiograph of chest as well as a CT image. Therefore, an unexpected CAD result is obtained thus lowering the ability of diagnosis.

The CAD system includes only one CAD algorithm for a given disease. Therefore, it is not possible to obtain a plurality of CAD data for a plurality of diseases. Therefore, if ten diseases are to be detected from one image based on the CAD data, the image data must be input to ten CAD systems and ten CAD data must be output. This increases the time and labor for the CAD operation.

A time for merely reading the image without outputting the CAD data is about three minutes. A time from requesting a kind of CAD operation to output the CAD data is about two minutes. If the CAD operation is performed during the reading, it takes a long time for reading and a difficulty occurs for the reading.

The CAD data includes many items, e.g., the position, type, and degree of the abnormality. In the conventional CAD system, all the items of data are output, thereby the output becomes complicated.

The CAD system does not store the CAD result, therefore, if the CAD operation is requested for the image which has been once analyzed, the same CAD operation is repeated thus wasting the time.

Meanwhile, a picture archiving communication system (hereinafter referred to as a PACS) for transferring, storing, and displaying the medical images has been developed. In the PACS, digital medical image data archived by modalities including a digitizer and attribute data thereof are transferred via a network and are stored in a large capacity recording means such as an optical disk device. Desired data are retrieved by using a data base system. The image data is transferred to a workstation via the network and is displayed However, the prior PACS does not function a CAD operation.

SUMMARY OF THE INVENTION

Accordingly, it is an object of the present invention to provide a computer-aided diagnosis system for medical use, which outputs computer-aided diagnosis data with a high precision by a simple operation having no adverse effect on diagnosis made by doctors.

Another object of the present invention is to provide a picture archiving communication system incorporating the computer-aided diagnosis system for medical use and having a high diagnosis precision.

According to one aspect of the present invention, there is provided a computer-aided diagnosis system comprising means for inputting a medical image and attribute data of the medical image, means for storing a plurality of computer-aided diagnosis algorithms, means for selecting, based on the attribute data, an optimum computer-aided diagnosis algorithm suitable for the medical image, means for analyzing the medical image using the optimum computer-aided diagnosis algorithm selected by said selecting means, and means for displaying an analysis result of said analyzing means.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 1 is a block diagram showing the arrangement of a first embodiment of a computer-aided diagnosis system for medical use according to the present invention;

FIG. 2 shows items of examination data;

FIG. 3 shows a practical example of the examination data for a conventional X-ray radiograph of chest;

FIG. 5 shows items of relevant data;

FIG. 6 shows a practical example of the relevant data;

FIG. 8 is a block diagram showing the arrangement of a data base shown in FIG. 1;

FIG. 9 shows an examination directory included in a data retrieving device shown in FIG. 8;

FIG. 15 shows a table registering the relationship between the name of a CAD algorithm and associated attribute data of the image which is applied with the CAD algorithm;

FIG. 16 is a view showing a practical example of ROI setting in lungs;

FIG. 17 is a block diagram schematically showing an algorithm for automatically setting an ROI;

FIG. 18 is a detailed block diagram for explaining the diagram of FIG. 16;

FIG. 28 shows a table for explaining an example of detailed naming of the abnormal positions;

FIG. 37 is a block diagram showing the arrangement of a sound output device as a main part of a third embodiment of the present invention;

FIGS. 38A and 38B show examples of a menu window display according to a seventh embodiment of the present invention;

FIG. 39 is a block diagram showing the arrangement of a computer-aided diagnosis system according to an eleventh embodiment of the present invention;

FIGS. 40A to 40E show modifications of marker display according to a twelfth embodiment;

FIG. 43 shows an example of a table formed of names of algorithms stored in a memory in a seventeenth embodiment of the present invention.

DETAILED DESCRIPTION OF THE PREFERRED EMBODIMENTS

Figure 4:
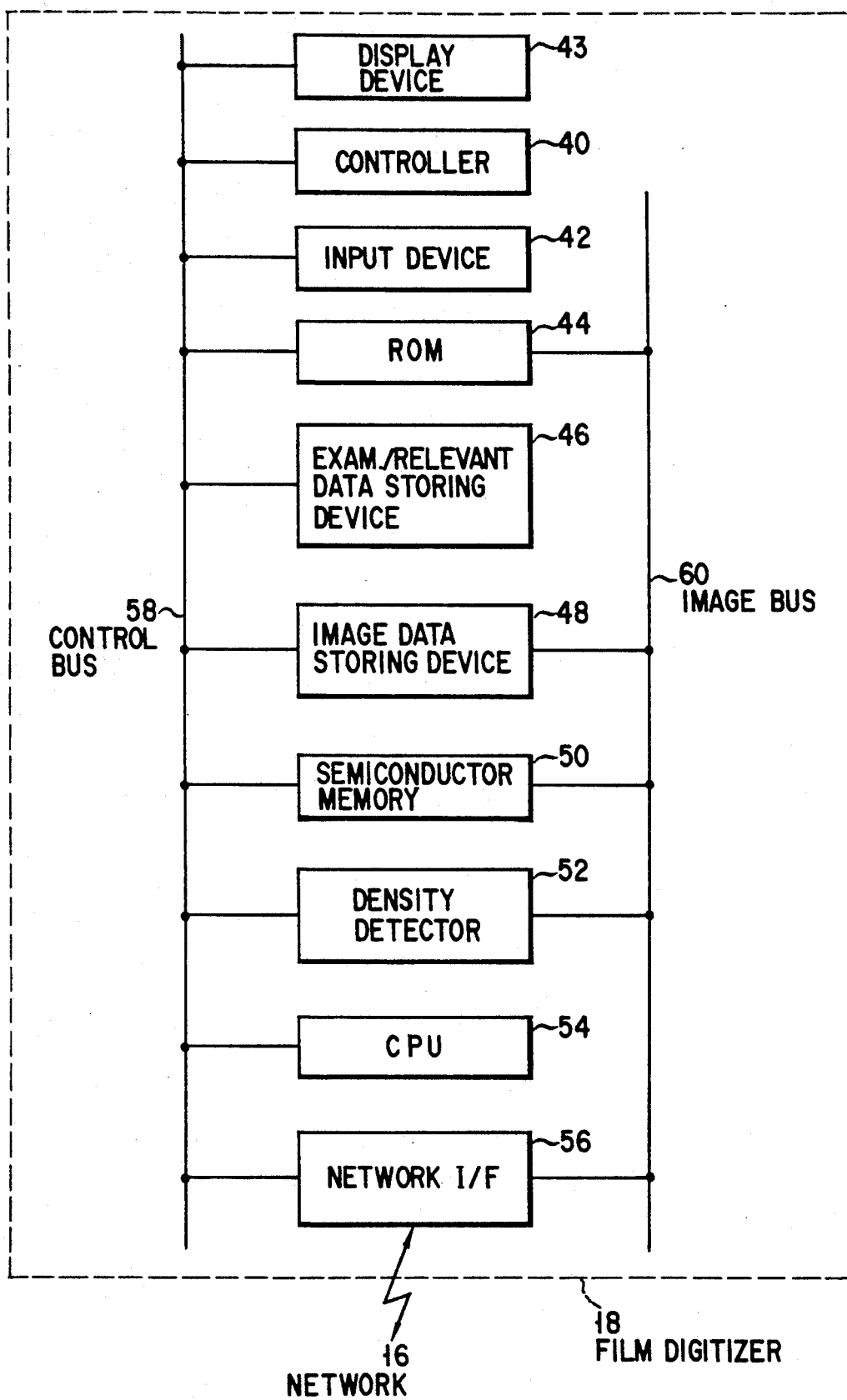
FIG. 4 is a block diagram showing the arrangement of a film digitizer shown in FIG. 1.

A preferred embodiment of a computer-aided diagnosis system for medical use according to the present invention will now be described with reference to the accompanying drawings. Though it is possible to embody the CAD system as a stand-alone system, an embodiment of the CAD system incorporated into the PACS will be described. FIG. 1 is a block diagram showing the first embodiment constructed on the basis of the PACS. In general, the PACS is a system for performing storage and transferring of various types of digital image data produced in a single or a plurality of hospitals, and is formed of an image data source 10 (hereinafter referred to as a modality), a data base 12, a workstation 14 as a display unit, and a network 16 for connecting these components.

The modality 10 includes various diagnosis devices for generating medical digital images, such as a film digitizer 18 for digitizing an image of an X-ray film obtained by an X-ray radiography apparatus, an angiography imaging apparatus 20, a computed tomography (CT) scanner 22, a magnetic resonance imaging (MRI) system 24, a nuclear medicine diagnosis apparatus 26, an ultrasound diagnosis apparatus 28, and an electric endoscope 30.

An examination ordering system 32 is also connected to the network 16 via a gateway 34. The examination ordering system 32 supplies examination data indicating details of examination on individual patients to the network 16. In this manner, the PACS performs control of data on the basis of correspondence between image data obtained by examination by the modality 10 and attribute data (including examination data, relevant data, and amend and/or update data for these data supplied from the workstation 14 and the data base 12). It is noted that the number of each of the modalities 10, the data base 12, and the workstation 14 are not limited to these of the above arrangement but can be increased or decreased as needed.

FIG. 2 shows an example of items of examination data input by the examination ordering system 32 and supplied to the network 16. An examination ID number is issued every time examination is performed. In the examination ordering system 32, such examination data is input by a doctor or a person in charge at the start of examination, and a technician of the modality executes examination on a patient upon receiving the examination request, thus obtaining image data. Each frame of the image data is associated with the relevant data. An example of the relevant data is shown in FIG. 5.

When, for example, radiographic examination using a conventional X-ray radiography apparatus is necessary, examination data as shown in FIG. 3 is input from the examination ordering system 32. A radiographic technician of the conventional X-ray radiography apparatus (not shown) takes conventional X-ray radiographs according to the input examination data. In the case of a conventional X-ray radiograph, digital image data can be obtained by digitizing the image of the X-ray film by the film digitizer 18. The image data, for example, consists of an array of data obtained by dividing the X-ray film into a matrix of 1,024×1,024 pixels and representing the density of each pixel by a digital number of 10-bit.

FIG. 4 shows the arrangement of the film digitizer 18. The film digitizer 18 comprises a controller 40, an input device 42, a display device 43, a read-only memory (ROM) 44, an examination/relevant data storing device 46, an image data storing device 48, a semiconductor memory 50, a film density detector 52, a central processing unit (CPU) 54, and a network interface (I/F) 56. Of these components, the controller 40, the input device 42, the display device 43, the ROM 44, the examination/relevant data storing device 46, the image data storing device 48, the semiconductor memory 50, the film density detector 52, the CPU 54, and the network I/F 56 are connected to a control bus line 58. The ROM 44, the image data storing device 48, the semiconductor memory 50, the film density detector 52, and the network I/F 56 are connected to an image bus line 60. The network I/F 56 is connected to the network 16.

The film density detector 52 divides an X-ray radiograph into a matrix of 1,024×1,024 pixels. The density detector 52 scans each pixel with a laser beam and measures the intensity of transmitted light to obtain the density of the pixel, thereby forming an intensity distribution of the transmitted light of the X-ray radiograph. This intensity distribution is converted into digital intensity data, and the data is supplied to the data storing device 48 through the image bus 60 and is stored therein as the image data. At the same time, examination data, together with relevant data, is stored in the examination/relevant data storing device 46. At this time, the display device 43 displays a prompt message for urging a technician to input an imaging direction of radiograph if the imaging direction is not input. When the text character denoting the imaging direction is input from the input device 42 such as a keyboard, this data is written in the column of the imaging direction of relevant data (FIG. 5) stored in the storing device 46.

Figure 7:
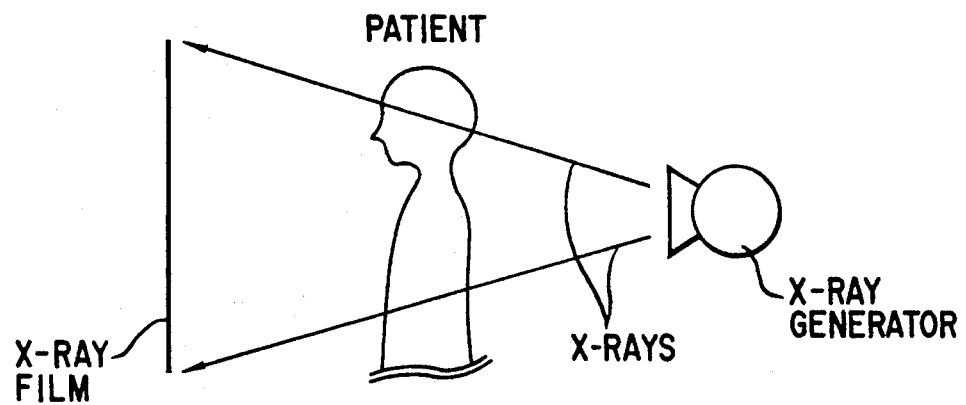
FIG. 7 is a view for defining an imaging direction in the conventional X-ray radiography.

FIG. 6 shows a practical example of the relevant data. The imaging direction of radiograph is defined, as shown in FIG. 7, such that when X-rays radiated from the back of a patient are detected on an X-ray film placed in front of the patient, the resulting image is referred to as a front image. Similarly, a right-side (left-side) image is defined as an image obtained when X-rays radiated from the left (right) side of the patient are detected on a X-ray film placed on the right (left) side of the patient. When digitizing of one frame of the X-ray radiograph is completed, the image data and the corresponding relevant data are associated with each other by means of the image ID number. The examination data and the corresponding relevant data are associated with each other by means of the examination ID number. The image data, the corresponding examination data, and the corresponding relevant data are supplied to the network 16 via the network I/F 56 and transferred to the data base 12 or the workstation 14 as data flowing through the network 16.

FIG. 8 shows the arrangement of the data base 12. The data base 12 comprises a CPU 62, a ROM 64, a semiconductor memory 66, a controller 68, a data retrieving device (including an examination directory) 70, a data compression circuit 71, an image data storing device 72, and a network interface (I/F) 74. Of these components, the CPU 62, the ROM 64, the semiconductor memory 66, the controller 68, the data retrieving device 70, the data compression circuit 71, the image data storing device 72, and the network I/F 74 are connected to a control bus line 76. The ROM 64, the semiconductor memory 66, the data compression circuit 71, the image data storing device 72, and the network I/F 74 are connected to an image bus line 78. The network I/F 74 is connected to the network 16.

The image data, the corresponding examination data, and the corresponding relevant data, which are flowing through the network 16, are input to the data base 12 via the network I/F 74, and stored in the image data storing device 72. If necessary, these data, particularly the image data is temporarily stored in the semiconductor memory 66 as a buffer memory. In this case, after the amount of the data is compressed to ½ or 1/10 by the data compression circuit 71, the data is stored in the image data storing device 72. The examination data and the relevant data are registered in the examination directory of the data retrieving device 70 to retrieve desired examination data and relevant data using an examination ID and read out items of data.

FIG. 9 shows an example of data contained in the examination directory of the data retrieving device 70 of the data base 12. Referring to FIG. 9, reference symbol N denotes the number of images obtained in one examination. The examination directory is formed of examination data (FIG. 2), address data for storing the reading report, amount of data of the reading report, and N number of image data included in the examination. Each of the image data is formed of address data for storing the relevant data, amount of data of the relevant data, address data for storing the image data, amount of image data, and first CAD result to n-th CAD result. The CAD result is formed of a CAD ID number and address data for storing the CAD result.

Next, an image reading operation performed by a doctor for the digital images whose attribute data are stored in the data base 12 as described above will be described. In hospitals, the image reading is performed to obtain a diagnosis result from medical images. The image reading in the PACS is that images are displayed on a display device such as a CRT of the workstation 14 and a doctor makes a diagnosis from the displayed images or X-ray film obtained in the conventional X-ray radiography examination.

Figures 10, 11:
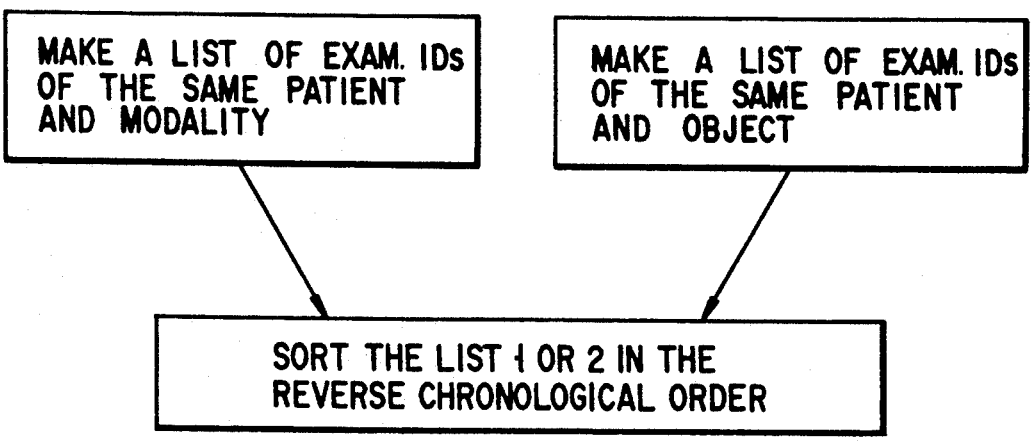
FIG. 10 shows the relationship between a doctor ID and a requesting doctor ID which is used when the image is transferred to a workstation at the time of reading.
FIG. 11 shows an operation for transferring the images which has been examined to the workstation at the time of reading.

When a doctor for image reading inputs his or her ID number with the power source of the workstation 14 ON, the workstation 14 is set ready for receiving an image reading request. This is the same procedure as the log-in operation in the conventional computer system. At this time, the workstation 14 sends a transfer request for images of a patient as an object to be image-read to the data base 12 on the basis of the examination ID input by the doctor or the examination ID which is registered in association with the doctor ID as shown in FIG. 10. If the patient has been examined, the workstation 14 may send a transfer request for images which have been read or viewed but are necessary to be referred as well as images which is not read or viewed. The necessary images are retrieved by means of, for example, the data base 12. All the examination IDs relating to the patient ID and the necessary image data are determined using a logical procedure, for example, as shown in FIG. 11. The examination IDs having the same patient and the same modality are retrieved to make a list of the examination IDs. Alternately, the examination IDs having the same patient and the same object are retrieved to make a list of the examination IDs. The examination IDs in one of the above two lists which has a high priority are sorted in the reverse chronological order.

The data base 12 selects images in units of examinations to be transferred by using the examination ID as a retrieval key. The selected image data in units of examinations or the compressed image data if the data is read out from the storing device 72, the relevant data, and the examination data in units of examinations are transferred to the network 16 via the network interface 74, and in turn to the workstation 14 sequentially.

A section for performing a CAD will be described below. The CAD is to obtain CAD data, for example, denoting a position of an abnormality in the image, by processing image data using a computer. In this embodiment, for example, the workstation 14 serves as a section for obtaining the CAD data.

Figure 12:
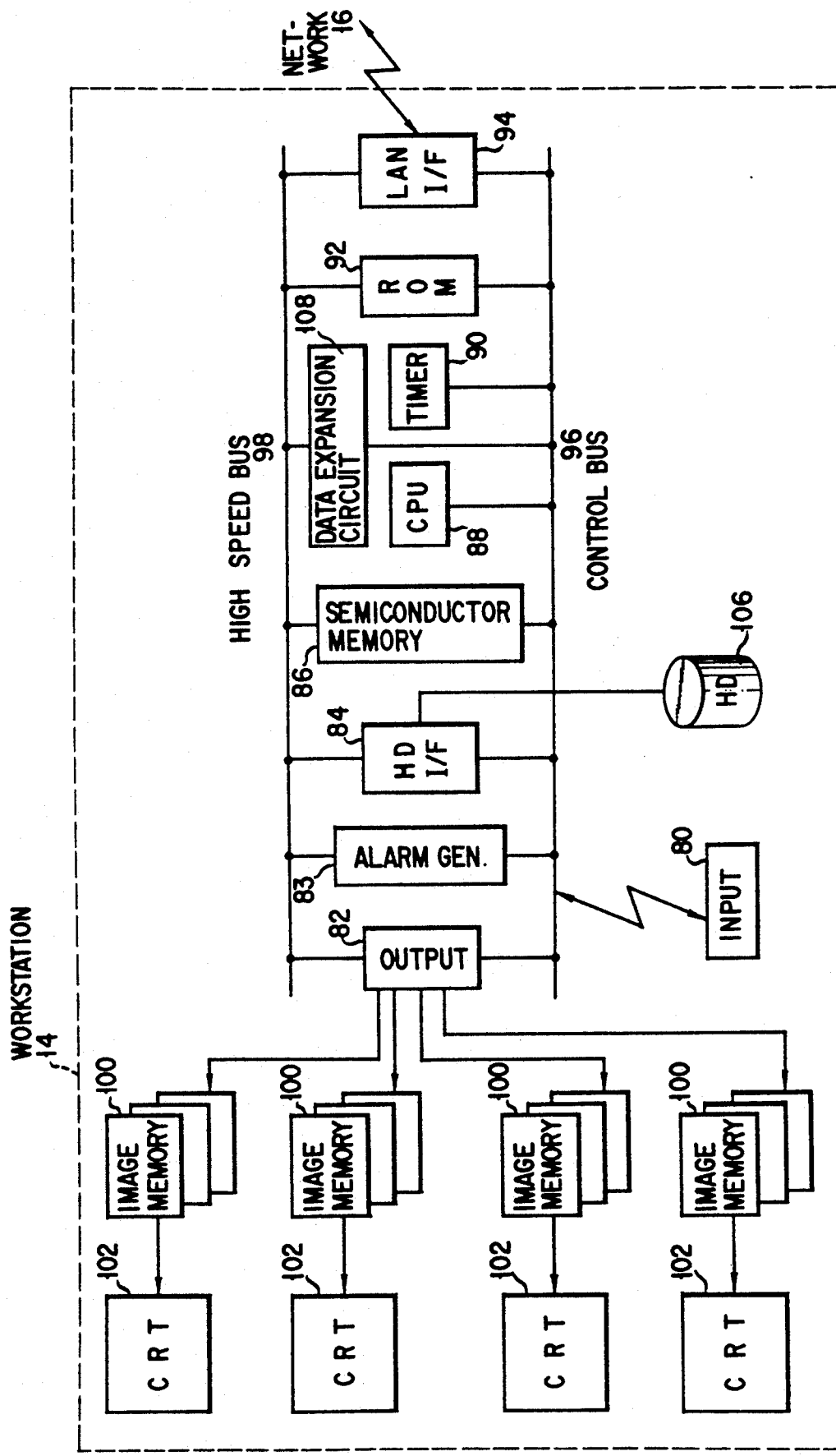
FIG. 12 is a block diagram showing the arrangement of the workstation shown in FIG. 1.

FIG. 12 shows the arrangement of the workstation 14. The workstation 14 comprises an input device 80, an output device 82, an alarm generator 83, a hard disk interface (HD I/F) 84, a semiconductor memory 86, a CPU 88, a timer 90, a ROM 92, a network interface (LAN I/F) 94, a plurality of image memories 100, a plurality of CRT displays 102, a hard disk unit (HD) 106, and a data expansion circuit 108. Of these components, the input device 80, the output device 82, the alarm generator 83, the HD I/F 84, the semiconductor memory 86, the CPU 88, the timer 90, the ROM 92, the LAN I/F 94, and the data expansion circuit 108 are connected to a control bus line 96. The output device 82, the alarm generator 83, the HD I/F 84, the semiconductor memory 86, the ROM 92, and the LAN I/F 94 are connected to a high speed bus line 98. The LAN I/F 94 is connected to the network 16.

The image memories 100 are provided in one-to-one correspondence with one or more (in this case, four) CRT displays 102. Each of the image memories 100 has two or three overlay screens (plane memories) and is connected to the output device 82. An output from the image memory 100 is displayed on the corresponding CRT display 102. The HD unit 106 is connected to the HD I/F 84. In the workstation 14, the image data input via the LAN I/F 94 in the form of the compressed image data, the corresponding relevant data, and the examination data in units of examinations are stored in the HD unit 106.

In order to perform an image reading, a doctor selects an image and the attribute data and the image is displayed on the CRT display 102 via the output device 82. The image to be displayed is selected among the images for one examination using the image ID input by the doctor. If the compressed image data is read out from the HD unit 106, the compressed data is expanded by the data expansion circuit 108 and then stored in the semiconductor memory 86. The relevant data and the examination data are also stored in the semiconductor memory 86. The image data is read out from the semiconductor memory 86 and is displayed on the CRT display 102 to be read or viewed by the doctor. For example, when an object to be image-read is a conventional X-ray radiograph, front and side images are usually displayed. When the patient has been examined, both non-read and past images (other than the non-read image; reference image) are usually displayed to perform comparative image reading.

Figures 13, 14:
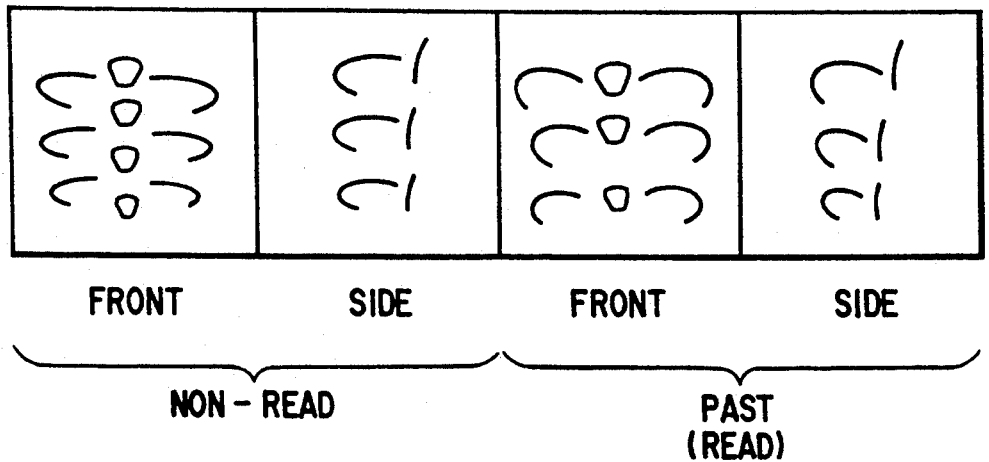
FIG. 13 shows an example of the images displayed on the workstation in the PACS at the time of diagnosis of the conventional X-ray radiograph.
FIG. 14 shows a CRT image display control table for managing the display of the workstation.

The manner in which the images are displayed on the CRTs is registered in a CRT image display control table as shown in FIG. 14. The table is formed by associating the examination ID and the image ID with the serial number of the CRTs. The table is stored in the semiconductor memory 86.

The image data which are sequentially transferred to the workstation 14 from the data base 12 are sequentially processed with a predetermined CAD algorithm.

A timing at which the CAD operation is started will be described below. After image data, examination data, and relevant data of one patient are transferred to the HD unit 106 of the workstation 14, the examination data and relevant data are read out sequentially from the HD unit 106 to the semiconductor memory 86 by the CPU 88.

Since the CAD operation is performed in which one of a plurality of different CAD algorithms suitable for the image data is selected, the ROM 92 includes a table indicating the name of a CAD algorithm and the items of the attribute data of the image data capable of being applied with the CAD algorithm, as shown in FIG. 15. The items of the attribute data of the image data to be analyzed and corresponding items of the attribute data of each CAD algorithm included in the table shown in FIG. 15 are compared with each other to determine whether or not the CAD algorithm can be applied to the image data. For example, a CAD algorithm for an interstitial lung disease is performed only when the modality is a conventional radiograph, the examination object is a chest, the imaging direction is a front, and the result of CAD is nothing. If the CAD, algorithm is not applied to the image data, nothing is stored in the item of the result of CAD. If other than nothing is stored in the item of the result of CAD, it means that the CAD algorithm is used for the image data. Therefore, since the examination data (FIG. 2) and the relevant data (FIG. 6) are already read out into the semiconductor memory 86, the items of modality and examination object are extracted from the examination data, and the items of imaging direction and result of CAD are extracted from the relevant data. These items are compared with items for each algorithm stored in the table shown in FIG. 15. The table of FIG. 15 is read out from the ROM 92 and is stored in the semiconductor memory 86. If they are equal to each other, the image is determined to be an object to which the CAD algorithm is to be applied. Therefore, an arithmetic operation of the CAD algorithm corresponding to the image data is started.

First, the image data determined to be an object to which the CAD algorithm is to be applied is read out into the semiconductor memory 86. The CPU 88 executes the CAD algorithm stored in the ROM 92 and stores the result of CAD in the semiconductor memory 86. The CPU 88 issues a serial number for the CAD ID and writes the CAD ID for retrieving the result of CAD in the item of the result of CAD in the relevant data (FIG. 6) stored in the semiconductor memory 86. The CPU 88 also writes the address storing the result of CAD in the relevant data. The default data of the address of the result of CAD is text data denoting nothing. When the operation for one CAD algorithm is ended, it is determined whether the next CAD algorithm can be applied to the image data.

The examples of the CAD algorithm written in the ROM 92 are as follows. A CAD algorithm for detecting a micro calcification in mammography is disclosed in Unexamined Japanese Patent Application No. 2-152443. A CAD algorithm for measuring the size of the heart and lung is disclosed in United States patent application Ser. No. 275,720 (filed Nov. 23, 1988). A CAD algorithm for detecting an interstitial lung disease is formed of the following algorithms:

1: An algorithm (which is schematically shown in FIG. 17, and illustrated in detail in FIG. 18) for setting ROIs (symbolized by □ in FIG. 16) for the CAD algorithm for one frame of the image data.

Figure 19:
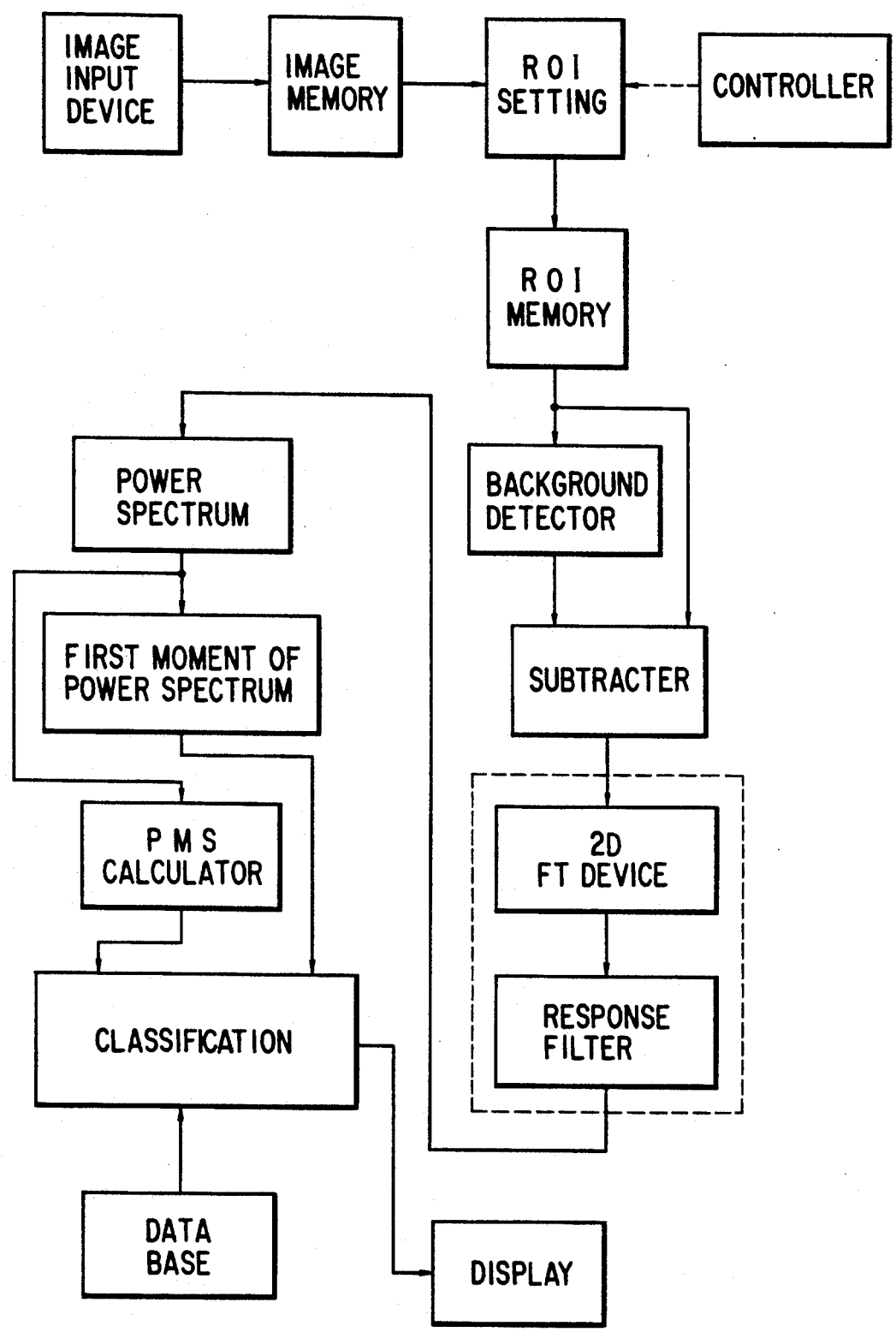
FIG. 19 is a block diagram schematically showing an algorithm for obtaining the amount of textures in the ROI.

2: An algorithm (which is schematically shown in FIG. 19) for calculating a physical amount of texture (which is an index indicating the magnitude and the length of period of a density variation in a texture pattern) in the ROI.

Figure 20:
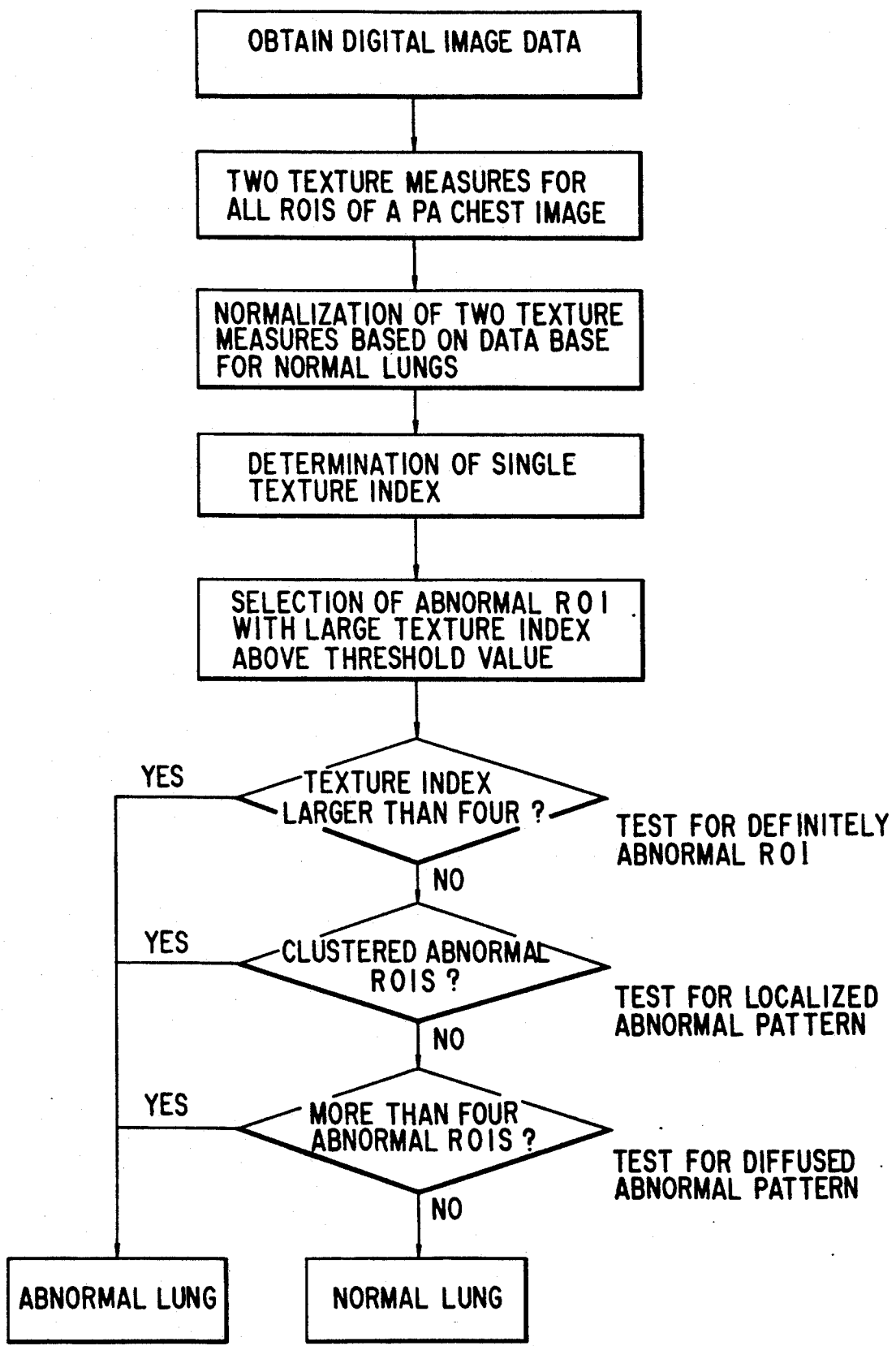
FIG. 20 is a flow chart schematically showing an algorithm for determining based on the amount of textures whether the ROI is normal or abnormal.
Figure 21:
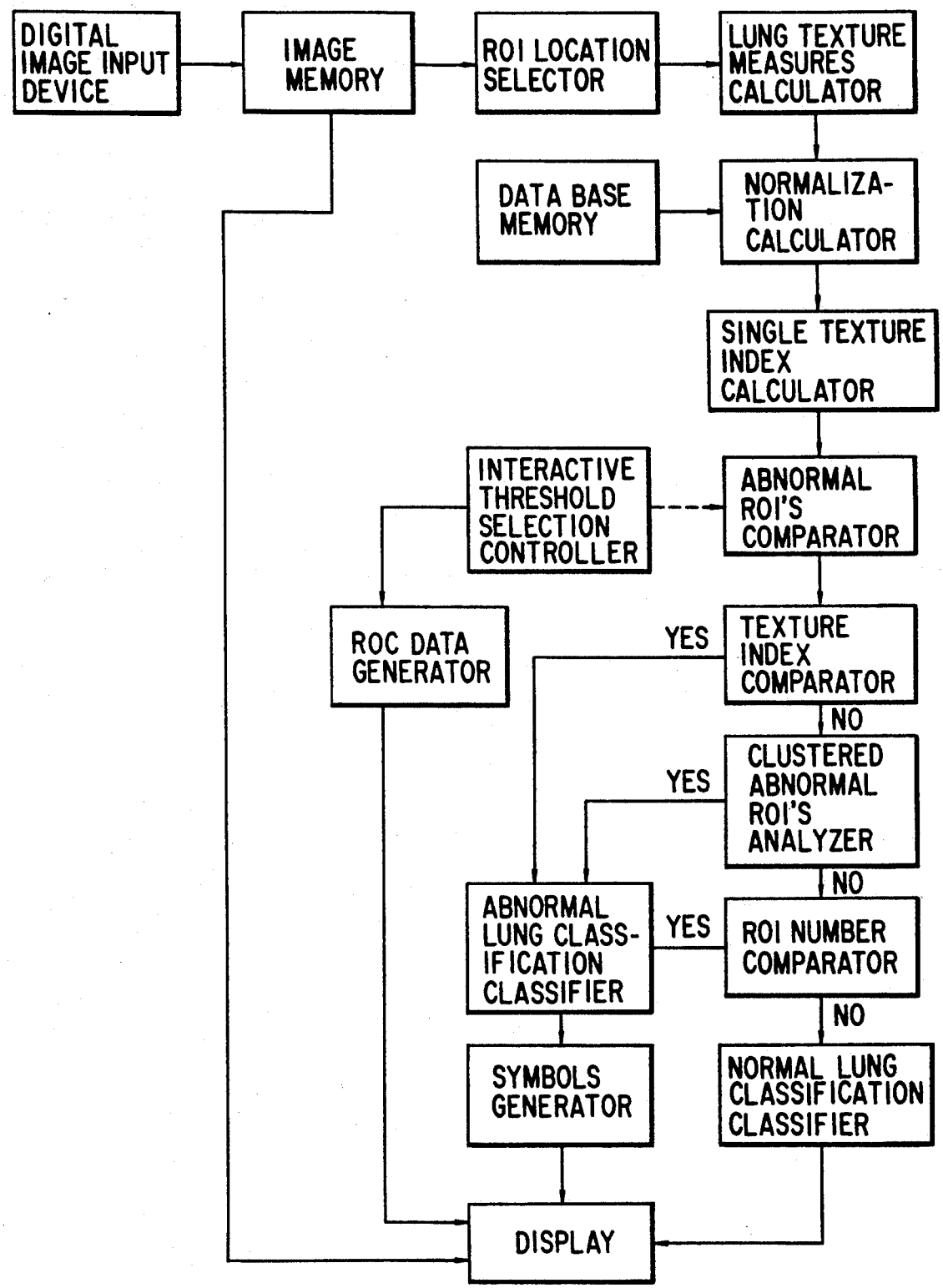
FIG. 21 is a block diagram performing the operation shown in FIG. 20.

3: An algorithm (the flow chart of which is shown in FIG. 20, and the arrangement in FIG. 21) for applying a threshold to the calculated physical amount of texture to determine abnormality or normality of the ROI.

Of these algorithms, the algorithms #1 and #2 are described in U.S. Pat. No. 4,851,984, and therefore a detailed description thereof will be omitted. In addition, since the algorithms #3 is described in U.S. Pat. No. 4,839,807, a detailed description thereof will be omitted.

Figures 22, 23:
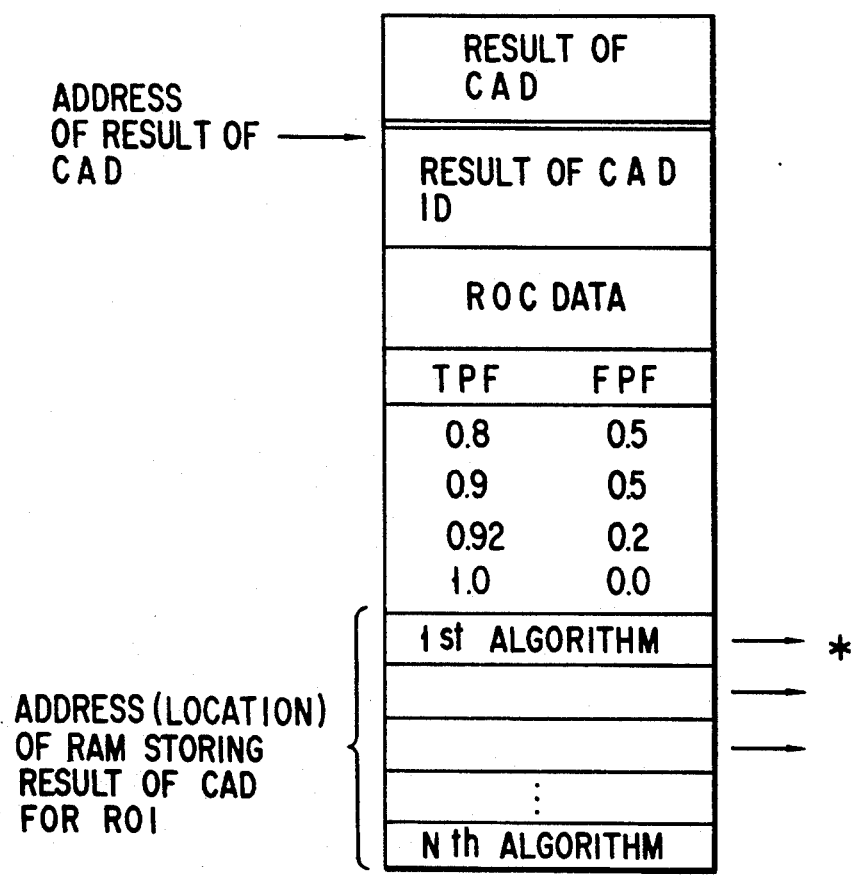
FIG. 22 shows an example of the data format of a CAD result.
FIG. 23 is a view showing a practical example of the CAD result data.

The results of the CAD algorithm and the classification of the normality are temporarily stored in the semiconductor memory 86. The detailed description for the case of the interstitial lung disease will be described. It is to be noted that "diffuse" is determined for those classified to be abnormal (i.e., those determined to be clustered abnormal ROIs in the flowchart shown in FIG. 20) because of the presence of clusters (grouped abnormal ROIs), and "local" is determined for abnormalities other than these; they are called patterns of abnormality. The pattern of abnormality is included as one item in the result of CAD of FIG. 22, and the type of pattern is written in this item as text characters, e.g., denoting local. FIG. 23 shows a practical example of the result of CAD in the case of an abnormal ROI. Here, a TPF represents a true positive fraction and an FPF represents a false positive fraction. failure. The ID of the result of CAD and the address of this CAD result data in the semiconductor memory 86 are additionally written as items in the relevant data (FIG. 5). When the result of CAD is stored in the data base 12, the ID and address are registered in the examination directory as shown in FIG. 9. The above operation is performed plural times if plural CAD algorithms can be applied to the image data. If plural results of CAD and addresses are obtained, all the plural IDs and addresses are stored in the examination directory.

The CAD result is output in response to application of an output request trigger. Therefore, while image reading is performed (a conventional X-ray radiograph of a chest is read or viewed in case of interstitial lung disease detection CAD), various commands including this output request must be input from the input device 80 of the workstation 14. In this embodiment, the description of the input device 80 will be given by using a touch panel type device. It is also possible to use a general device, such as a keyboard as the input device 80.

Figure 24:
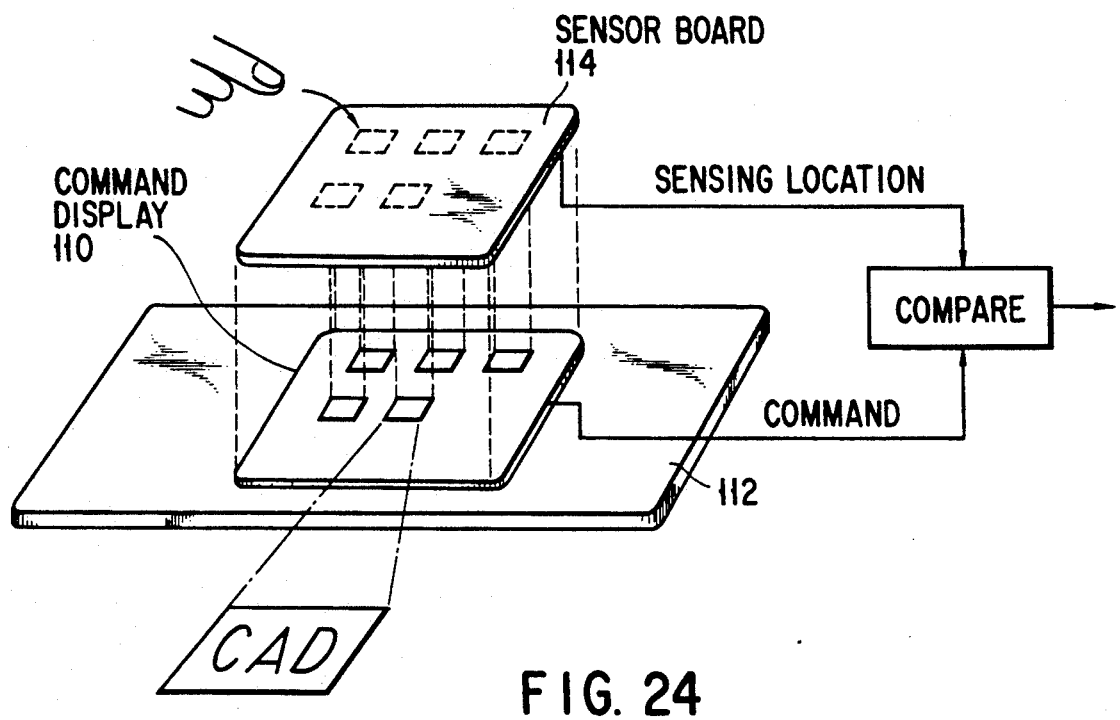
FIG. 24 is a perspective view showing a touch panel as an example of an input device of the workstation.

FIG. 24 shows an example of the input device 80. This touch panel comprises a command display 110 on which the names of commands is displayed, a panel 112 on which the command display 110 is arranged, and a transparent sensor board 114 located on the command display 110. When a position corresponding to the name of a command is selectively touched with a finger, the sensor board 114 senses the touched portion.

Figure 25:
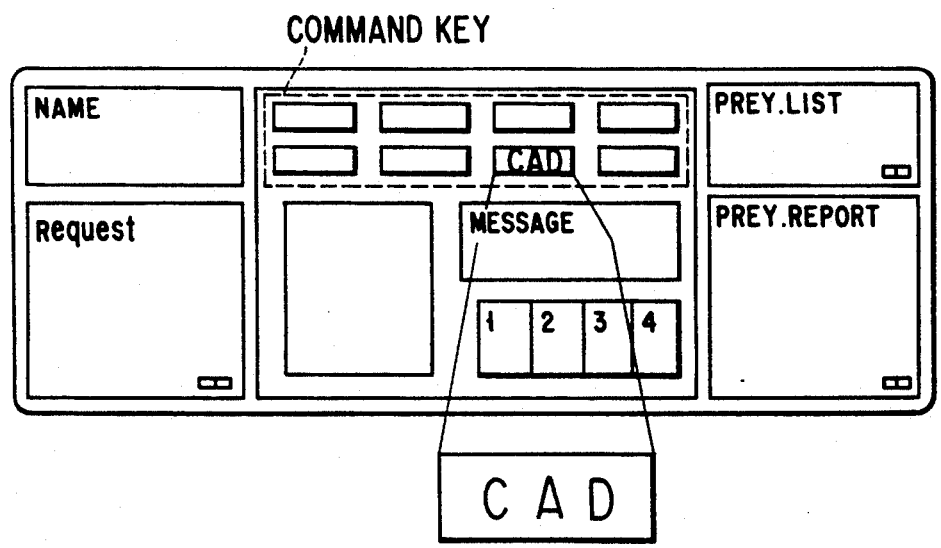
FIG. 25 is a view showing a display example of the touch panel.

When, for example, several command buttons are displayed on the output device, an operator can recognize a command display through the sensor board 114. The operator selects a command by touching the sensor board 114, thus executing the command. A button (CAD button shown in FIG. 25) for requesting an output of a result of CAD is prepared (displayed) on the touch panel. Detecting depression on this CAD button on the touch panel is a trigger for requesting the CAD result output.

Since the CAD result can be output in various modes, the mode of outputting the CAD result is determined next. The CPU 88 reads out the relevant data (FIG. 6) corresponding to the examination ID and image ID included in the CRT image display control table (FIG. 14). Further, the CPU 88 reads out the CAD result ID and CAD result address from this relevant data, thereby reading out or retrieves the result of CAD (FIG. 22).

An example of CAD result output is described below. The CPU 88 starts the program in the ROM 92 and outputs a CAD result (FIG. 23) relating to the abnormality to a corresponding output device according to the pattern of the abnormality. In this program, the item of data denoting the pattern of abnormality is extracted from the result of CAD (FIG. 23) relating to the abnormality and stored in the semiconductor memory 86. If the pattern of abnormality is a diffused pattern, a text sentence generator is activated in order to output an abnormality alarm in the form of a text sentence. If the pattern of abnormality indicates local, the alarm (marker) generator 83 is activated in order to indicate the location of abnormality by means of a marker.

Figure 26:
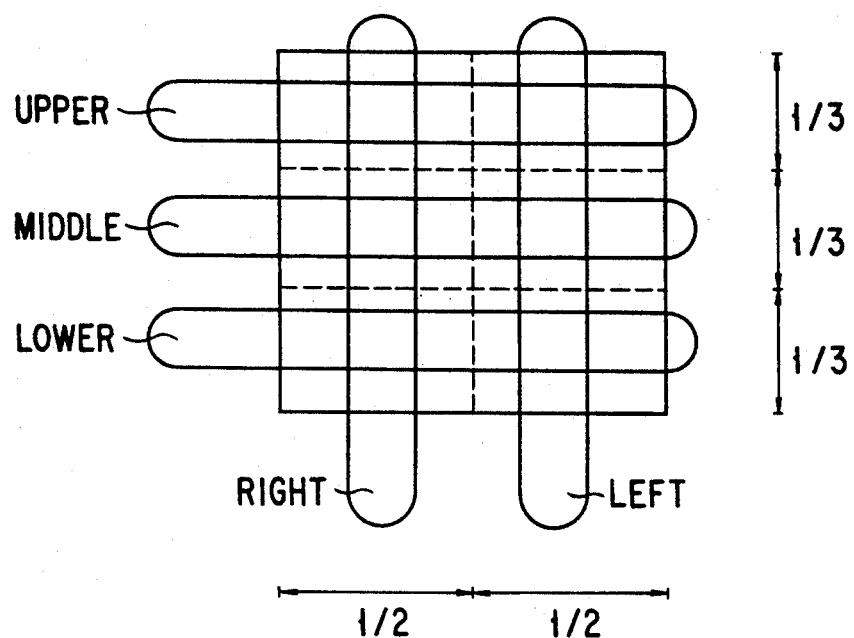
FIG. 26 is a view for explaining an example of a schematic naming of abnormal positions.
Figure 27:
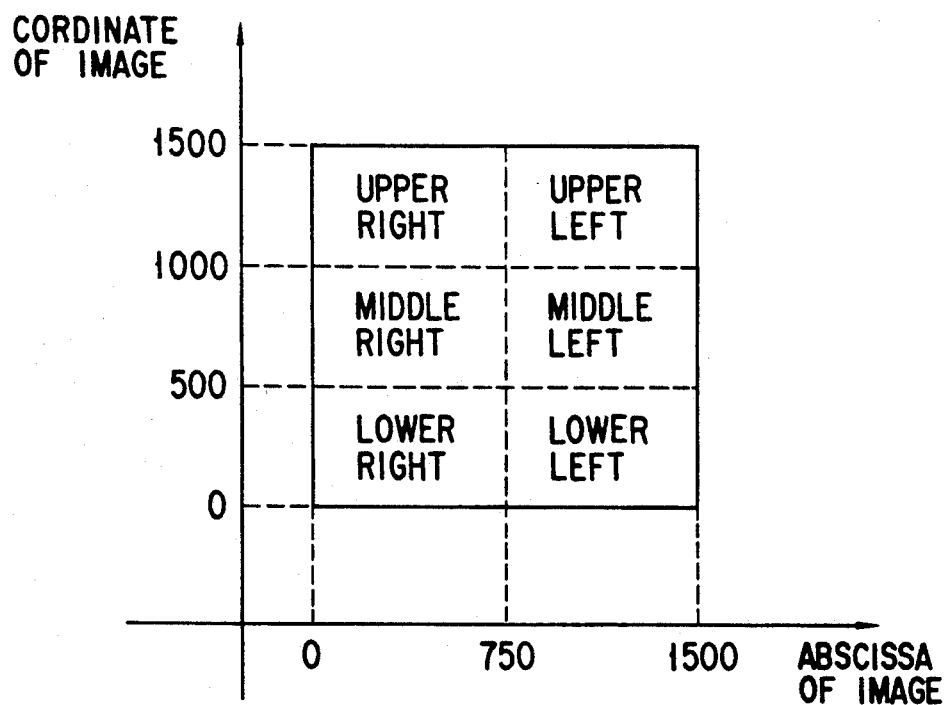
FIG. 27 shows a relationship between locations and coordinates of the abnormal positions.
Figure 29:
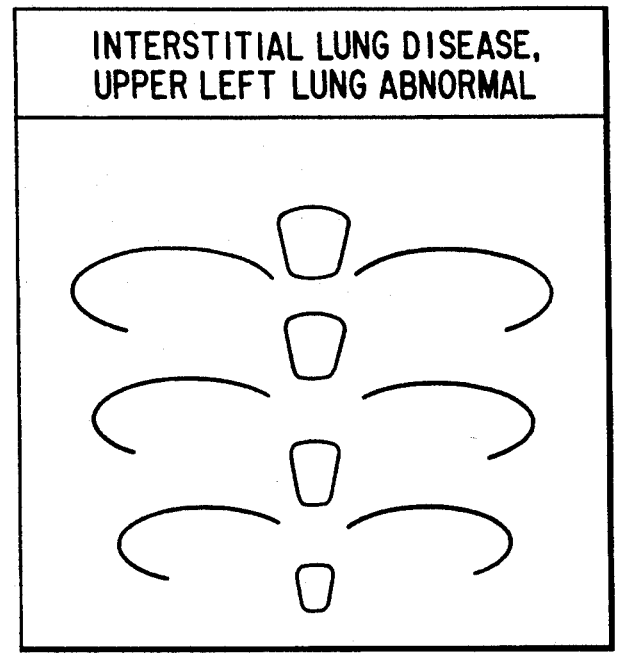
FIG. 29 shows an example of a text sentence display.

In this case, the text sentence represents the location of abnormality on an image by means of words, thereby making an alarm. For this purpose, as shown in FIG. 26, a screen of the display is equally divided into six regions in advance, and a name is assigned to each region. A table (FIG. 27) showing a correspondence between the names and the x, y coordinates of the regions is stored in the ROM 92. The right and left is defined as viewed from the patient. The CPU 88 starts the program in the ROM 92. In this program, the x, y coordinates of the location of the abnormal ROI is extracted from the CAD result and an expression of abnormality is read out from the table shown in FIG. 28 and stored in the ROM 92 in accordance with the location of the abnormality. The readout expression data is stored in the semiconductor memory 86 to be inserted into the text sentence. If plural CAD results are obtained, the above operation is repeated for the number of the CAD results. The text sentence is, for example, "interstitial lung disease, upper right lung abnormal." In this case, the expression of the underlined portion changes in accordance with an abnormal portion. Subsequently, character string data of the text sentence is converted into dot patterns in units of characters. Thereafter, with reference to the CRT image display control table (FIG. 14), one text line (white) is provided in the uppermost stage of an image memory 100 (overlay screen) corresponding to the CRT displaying the image, and dot patterns of black characters are stored in the text line of the image memory 100, as shown in FIG. 29.

Figure 30:
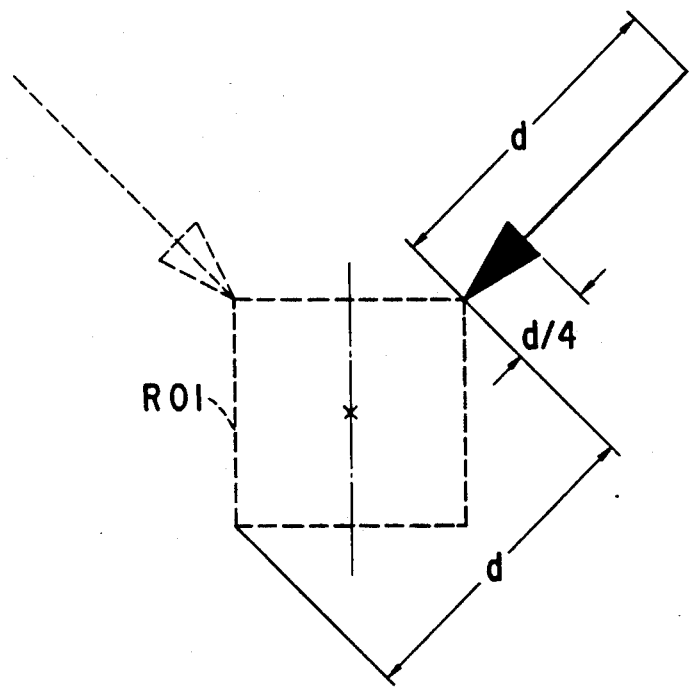
FIG. 30 shows an example of marker display.

The marker is a means for representing the location of abnormality on an image by using an arrow. The CPU 88 of the workstation 14 starts the program in the ROM 92 and reads out the location of abnormality from the CAD result data (FIG. 22), thus forming the shape of a marker as shown in FIG. 29, based on a font pattern of the ROM 92. In this case, although d (diagonal of the square)=1.5 cm is preferable, d is not limited to this value but can be changed freely. The screen is divided into right and left portions as viewed from the operator. If the location (the center of ROI indicated by a symbol X) of abnormality is present on the right side of the screen, the arrow shown in FIG. 30 is converted directly into a bit pattern. If, by contrast, the location is present on the left side, the arrow of FIG. 30 is inverted symmetrically about a longitudinal line (alternate long and short dashed line in FIG. 30) including the center of ROI, i.e., in a mirrorlike manner and the resulting mirror image of the arrow as indicated by a broken line in FIG. 30 is converted into a bit pattern.

In addition, the bit pattern data is written in a location corresponding to the position of abnormality in the image memory 100 (overlay memory) corresponding to the CRT displaying the image. If a plural CAD results are obtained, the above operation is repeated until all the CAD results are read out and written into the overlay memory. The data in the image memory 100 (overlay memory) is displayed on the CRT overlapped with the image data. The display color of the bit pattern data of the marker is switched between black and white in synchronism with the timer 90. Thus, the effect of alarming of the marker is enhanced. It is noted that the period of switching is 2 Hz.

At this time, though all the CAD results are simultaneously displayed on the CRT, some of them may be selectively displayed. The names of buttons displayed on the touch panel are changed in accordance with the needs of the operator. For example, the names of the buttons are changed in accordance with the CAD algorithm now applying to the image data. A label "ID", "MC", and "BH" are provided for buttons in case of an interstitial lung disease detection CAD, micro calcification detection CAD, and heart size measuring CAD. When a CAD algorithm is selected, the CAD result corresponding to the algorithm is written in the overlay memory and the other results are deleted from the overlay memory.

Another mode of CAD result output will be described in which the CAD result has a hierarchical structure. That is, a summary of the CAD result is output first by means of, e.g., the text sentence and the marker as described above, and then details are output. For this purpose, a button for requesting a CAD detail output is prepared on the input device (touch panel) 80 (FIG. 25) of the workstation 14. In other words, the names of buttons on the touch panel are changed in accordance with the application used by an operator. When depression on the CAD detail output button on the touch panel is sensed while the text sentence and the marker are displayed, a trigger for requesting an output of the CAD detailed result is generated.

The output of the CAD detailed result will be described below. It is assumed that the text sentence is already formed and stored in the form of black characters on a white background as shown in FIG. 29 in the image memory 100 (overlay screen). The CPU 88 starts the program in the ROM 92 to read out the CAD result data (FIG. 22) from the semiconductor memory 86. The CPU 88 forms an arrow marker for data having abnormality independently of the pattern of the abnormality. The marker indicates the location of the abnormality on an image by means of an arrow.

Figure 31:
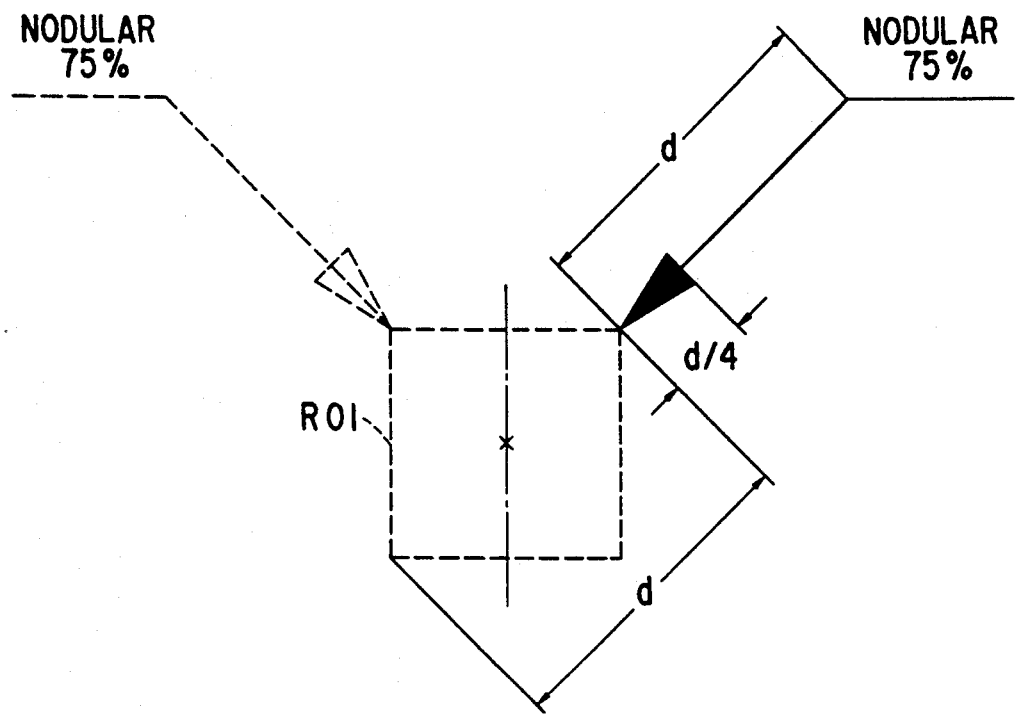
FIG. 31 shows an example of detailed CAD display using the marker shown in FIG. 30.

The CPU 88 reads out the location of the abnormality and forms the shape of the marker as shown in FIG. 31, based on the font pattern in the ROM 92. At this time, the screen is divided into right and left portions. If the abnormality location is present on the right side viewed from the operator, the arrow of FIG. 31 is converted directly into a bit pattern. If, on the other hand, the abnormality location is present on the left side, the arrow of FIG. 31 is mirrorlike-inverted symmetrically about a longitudinal line (alternate long and short dashed line in FIG. 31) including the location of the abnormality, and the resultant mirrorlike arrow as indicated by a broken line in FIG. 31 is converted into a bit pattern. In addition, the type (e.g., nodular) and the degree (e.g., 75%) of the abnormality are read out from the CAD result data and are converted into a bit pattern, as shown in FIG. 31. Unlike the bit pattern of the arrow, the bit pattern of characters of the type and degree is not mirrorlike-inverted regardless of whether the abnormality location is present on the right side or the left side.

This bit pattern data is written in a location corresponding to the position of the abnormality in the image memory 100 (overlay screen) corresponding to the CRT 102 displaying the image. As a result, the arrow marker associated with the characters indicating the type and the degree of the abnormality (FIG. 31) is displayed, together with the text sentence shown in FIG. 29, on the screen.

The data in the image memory 100 (overlay screen) is displayed overlapped on the examination image. At this time, the color of the data display on the overlay screen is switched between black and white in synchronism with the timer 90. The period of switching is 2 Hz.

An example of an option output of the CAD detailed result will be described below. As in the case of the trigger for the detailed output, a button for requesting a detailed option output of the CAD result is displayed on the input device (touch panel) 80 of the workstation 14 as a trigger for the option output. When depression on the CAD detailed option output button on the touch panel is sensed while the detailed output is performed, the trigger for requesting the CAD detailed option output is attained.

It is supposed that the text sentence is already formed and stored in the form of black characters on a white background as shown in FIG. 29 in the image memory 100 (overlay screen). The CPU 88 starts the program in the ROM 92 to read out the CAD result data (FIG. 22) from the semiconductor memory 86 and forms an arrow marker for data having abnormality independently of the pattern of the abnormality. This marker represents the location of the abnormality on the image by means of an arrow.

Figure 32:
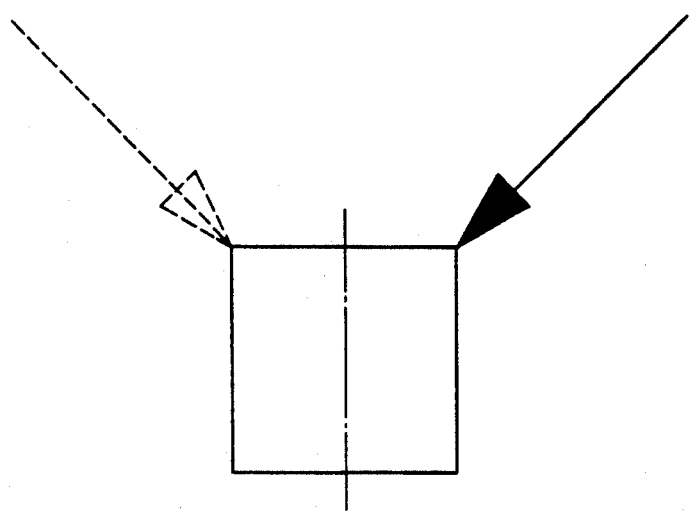
FIG. 32 shows another example of the marker display.

The CPU 88 reads out the location of the abnormality and forms an arrow marker and a square ROI marker, as shown in FIG. 32, based on the font pattern of the ROM 92. Here, the screen is divided into right and left portions. If the abnormality location is present on the right side, the arrow and the ROI of FIG. 32 are converted directly into bit patterns. If the location is present on the left side, the arrow of FIG. 32 is inverted in a mirrorlike manner, and the resulting arrow indicated by a broken line in FIG. 32 and the ROI are converted into bit patterns. This bit pattern data is written in the location corresponding to the position of the abnormality in the image memory 100 (overlay screen) corresponding to the CRT displaying the image in the CRT display image control table (FIG. 12).

The data in the image memory 100 (overlay screen) is displayed overlapped on the examination image. At this time, the color of the data display on the overlay screen is switched between black and white in synchronism with the timer 90. The period of switching is 2 Hz.

Figure 33:
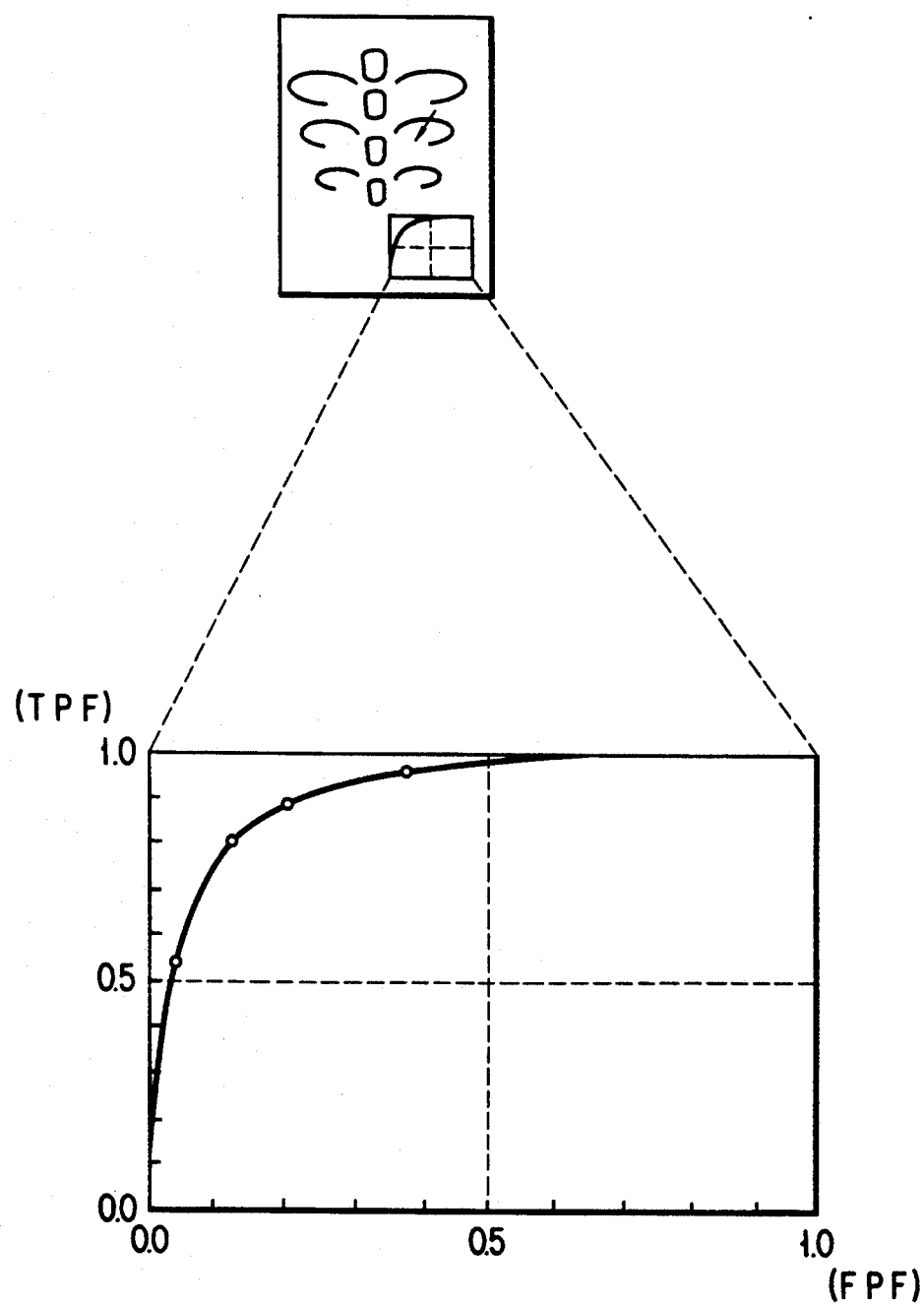
FIG. 33 shows an ROC curve display as an optional CAD output.

Another example of the option output will be described. When another option output is requested, the CPU 88 starts a given program in the ROM 92 to read out ROC (Receiver Operator Curve) data included in the CAD result from the semiconductor memory 86, thus forming an ROC curve. As shown in FIG. 33, the ROC curve is one of examples for indicating the ability of CAD and is so formed as to be fitted in a portion below and to the right of the image. In the ROC curve, the abscissa denotes the FPF and the ordinate denotes the TPF. The ROC curve is converted into a bit pattern. The bit pattern data is written in the image memory 100 (overlay screen) corresponding to the CRT displaying the image. The data in the image memory (overlay memory) 100 is displayed on the CRT overlapped with the examination image.

An example of a request trigger for ending the output of the CAD result will be described below. When the image reading of a conventional X-ray radiograph of a chest is performed and the image and the CAD result are displayed on a CRT screen, the trigger for ending the CAD result output is automatically generated upon stopping the image display in order to display another image. When the output is ended, the image display is continued, and only the display on the overlay screen is turned off. Further, the touch panel may include a button for providing the command representing the end of the image reading and the relevant data is updated as being read if the button is depressed.

A command for requesting the end of the CAD output can also be applied from the input device 80 of touch panel type.

Figure 34:
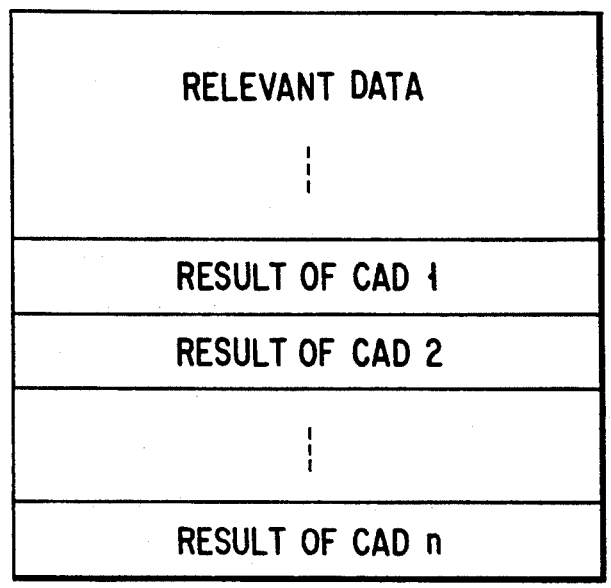
FIG. 34 shows the data format of a CAD result.
Figure 35:
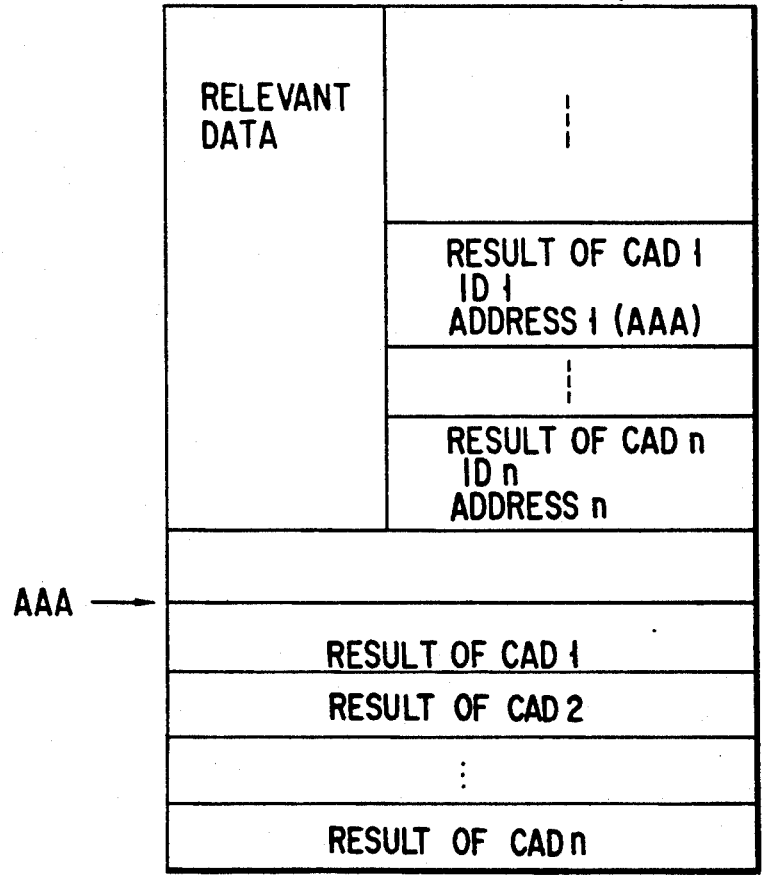
FIG. 35 shows a practical example of the CAD result.

It is to be noted that the CAD data is preferably stored even when its output (display) is stopped. The CAD result is added to the updated relevant data, as shown in FIG. 34, and supplied to the data base 12 to be stored therein. In the data base 12, all the CAD IDs and CAD result addresses in the relevant data are stored in the examination directory (FIG. 9). In a subsequent image reading, if an image transfer request is supplied to the data base 12, the image data and the corresponding examination and relevant data are transferred by the network 16 and stored in the semiconductor memory 86 of the workstation 14. At the same time, the CAD result ID is read out and all the CAD results are retrieved based on the CAD IDs. In this case, as shown in FIG. 35, the address of the CAD result written in the relevant data is converted into the address on the semiconductor memory 86 and is stored in the relevant data.

According to this embodiment as has been described above, the following effects can be obtained. That is, in addition to a medical image, CAD data concerning the image is also displayed. Therefore, an erroneous diagnosis due to an oversight of a disease can be prevented in medical image diagnosis, thus increasing diagnosis precision. Labors can be reduced in a diagnosis operation performed by a doctor (operator). In medical image diagnosis, particularly in an image reading operation, an erroneous diagnosis caused by an oversight of a disease can be prevented to improve diagnosis precision. Since the CAD data is obtained by analyzing medical images using a computer, objective and quantitative results can be obtained. Therefore, it is possible to prevent an erroneous diagnosis which is a result of subjective determination by a human being, and consequently diagnosis precision can be increased. In medical image diagnosis, a doctor who is not an expert of an image of interest sometimes cannot make a satisfactory diagnosis. According to the present invention, diagnosis precision can be improved also in this case.

As the CAD data, the position, the type, or the degree of abnormality is displayed, so that the abnormality can be readily recognized. As a result, an erroneous diagnosis caused by an oversight of a disease can be prevented to improve diagnosis precision.

Arithmetic operation calculating the CAD data is started by a computer before an output request for the CAD data is generated. Therefore, it is possible to shorten a time from generating the output request to displaying the CAD data.

When several algorithms for obtaining CAD data are available, an inappropriate processing is performed for an image data of interest unless the image data is correctly assigned to the algorithm, and erroneous CAD data results. According to this embodiment, however, since a suitable algorithm is selected for each image, output of erroneous CAD data can be prevented to increase diagnosis precision.

Since the CAD result is stored in the data base 12, an image which is diagnosed once need not be analyzed again.

A CAD algorithm is determined for each diagnosis of interest, and the algorithms are selectively executed in accordance with each object. Therefore, it is possible to prevent a production of CAD data which may cause an erroneous diagnosis in the case when an unsuitable algorithm is applied to an object. Further, the attribute data includes the modality, the examining object, and the imaging direction, and an algorithm is executed when these items of the attribute data coincide with those of an object image of the algorithm. Therefore, an unsuitable algorithm is not applied to the image.

An alarming means which strongly attracts attention of the doctor is used as a means for alarming abnormality. Therefore, an erroneous diagnosis due to an oversight can be prevented to increase diagnosis precision. An optimal alarming means is selected to attract attention in accordance with the type of abnormality. Therefore, it is possible to prevent an erroneous diagnosis caused by an oversight, thus improving diagnosis precision. By flickering the alarm display, the alarming means strongly attracts attention to prevent an erroneous diagnosis resulting from an oversight, thus improving diagnosis precision.

The CAD data is hierarchically constructed and output gradually from its summary to details. Therefore, a large number of different types of CAD data are not simultaneously displayed to cause a cumbersome operation. Thus, an erroneous diagnosis can be prevented to increase diagnosis precision. For example, the position of abnormality alone is output first as the CAD data. If the abnormality cannot be clearly determined, a doctor freely makes output requests for, e.g., the degree, the type, and the pattern of the abnormality, thus avoiding a cumbersome operation to increase diagnosis precision. In this case, a usable command (button) is prepared for each level (hierarchical level) of contents at which the CAD data is output. Since a user need only select a command of interest from the prepared commands, a labor for selecting from a large number of commands is reduced.

Before application of the CAD algorithm to a given image data, it is determined whether the CAD algorithm can be applied to the image data based on the attribute data of the image data and only the algorithm which is determined to be able to apply to the image data is applied to the image data. Therefore, it is possible to prevent lowering the quality and precision of diagnosis due to the output of the erroneous CAD data.

The CAD system according to the present invention is described as being incorporated into the PACS. However, it is possible to realize a stand-alone type CAD system according to the present invention.

Plural CAD algorithms are stored in the system and an optimum one is automatically selected based on the relevant data of the object image data. Therefore, it is possible to reduce the labors of the doctor for selecting the suitable algorithm, inputting the respective image data, and outputting the respective CAD data.

The computer starts an arithmetic operation for calculating the CAD data before an output request for the CAD data is generated. Therefore, it is possible to shorten a time from generating the output request to displaying the CAD data.

The numerical data denoting the CAD result includes many items. If all the data are output, the output becomes complicated. According to the first embodiment, the CAD data are stored in the form of a table and only desired data is output by retrieving the data from the table using the retrieval key corresponding to the desired condition. Therefore, the CAD result can be output in a simple form.

The attribute data includes an item of data denoting whether or not the image data has been read or viewed. Based on this attribute data, the CAD result of the image data which has been read or viewed is not output. Therefore, it is possible to prevent a confusion in which the CAD result different from the reading report is output. Based on this attribute data, only the image data which has not been read or viewed is analyzed using the CAD algorithm. Therefore, a time from generating the output request to displaying the CAD data becomes shorter than that in the case of all the image data are analyzed. Further, the attribute data includes an item of data representing the CAD result and the image data which has been analyzed is not analyzed again. Therefore, it is possible to further shorten a time from generating the output request to displaying the CAD data.

Other embodiments of the present invention will be described below.

Figure 36:
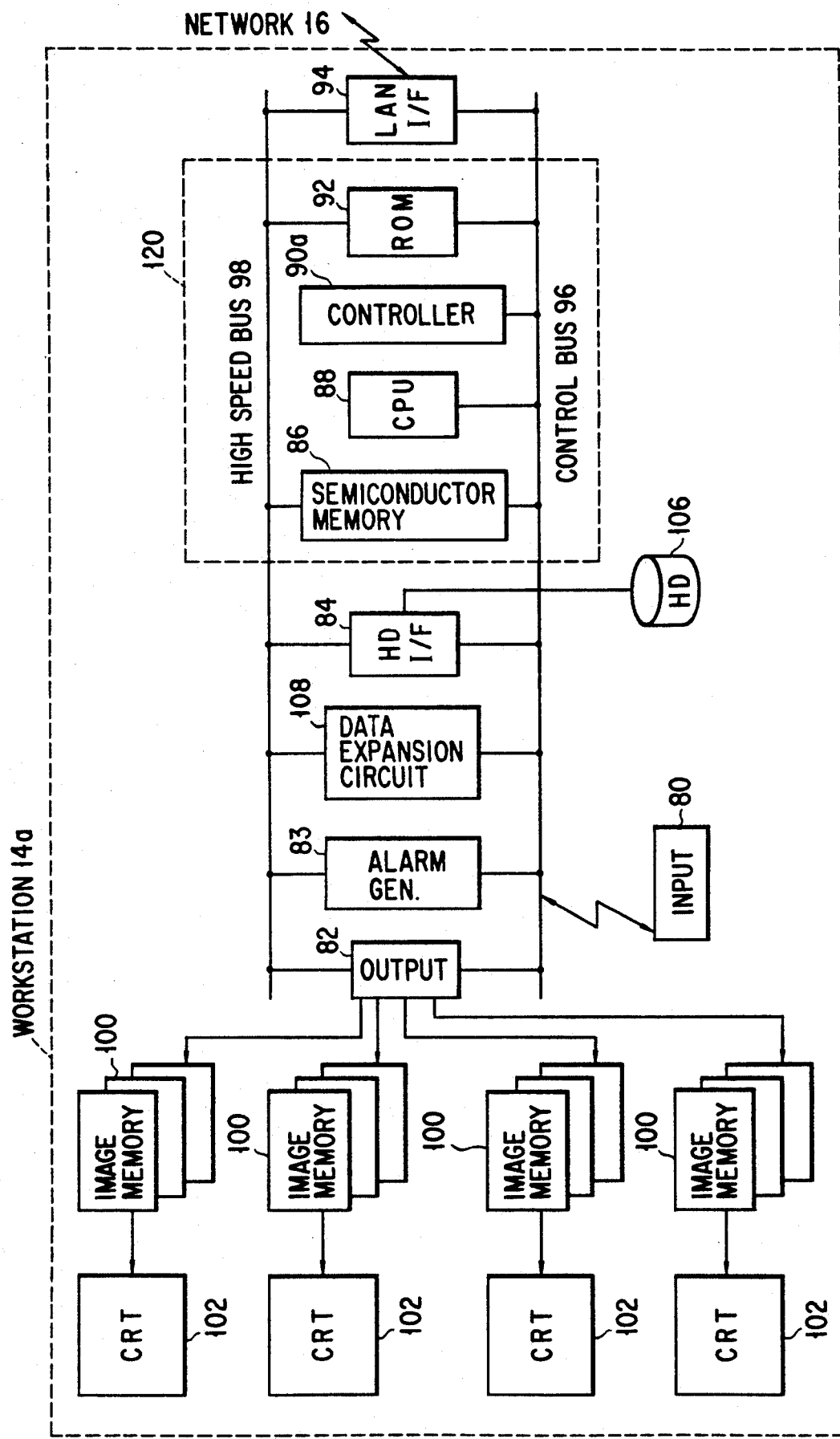
FIG. 36 is a block diagram showing the arrangement of a CAD processor included in a second embodiment of a computer-aided diagnosis system for medical use according to the present invention.
Figure 41A:
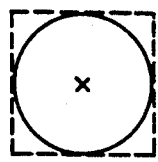
FIGS. 41A to 41F show other modifications of the marker display according to the twelfth embodiment.
Figure 41B:
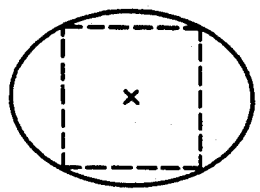
Figure 41C:
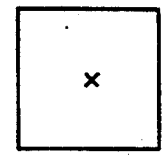
Figure 41D:
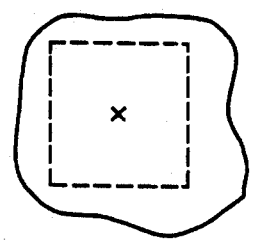
Figure 41E:
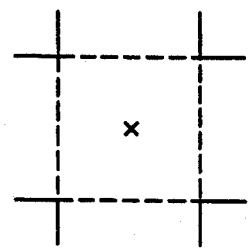
Figure 41F:
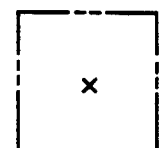

A second embodiment comprises, in addition to the workstation 14 for displaying the image as shown in FIG. 12, a workstation 14a having a CAD processor 120 as shown in FIG. 36. This workstation 14a for obtaining CAD data is different from the workstation 14 in that a controller 90a is provided in place of the timer 90. In terms of an operation, the second embodiment is different from the first embodiment in a timing at which a CAD arithmetic operation is started.

In the second embodiment, when image data, examination data, and relevant data of one patient are transferred to the HD unit 106 of the workstation 14a, the examination data and the relevant data are read out sequentially from the HD unit 106 into the semiconductor memory 86 by the CPU 88. The ROM 92 stores the table denoting the relationship between the name of the CAD algorithm and the attribute data of the image data which can be adapted to the CAD algorithm as shown in FIG. 15. Therefore, since the examination data (FIG. 2) and the relevant data (FIG. 6) are already read out into the semiconductor memory 86, the modality and the examining object are read out from the examination data, and the imaging direction is read out from the relevant data. These read out items of data are stored in the semiconductor memory 86. These items of data are compared with the attribute data of the image stored in the table (FIG. 15) of the ROM 92.

If these items coincide with those of a given CAD algorithm, e.g., interstitial lung disease detection CAD, this image is determined to be an image to which the interstitial lung disease detection CAD algorithm can be applied, and the operation of the CAD is started. At this time, the CPU 88 in the workstation 14a designates activation of the CAD processor 120 (FIG. 36), and supplies input data to the processor 120. The input data given to the CAD processor 120 includes the image data, the examination data, and the relevant data. The CAD processor 120 has its own CPU, and by means of the CPU it executes the CAD operation and outputs a CAD result. The CAD result is temporarily stored in the memory as data having the format shown in FIG. 22. In addition, the ID and the address of the CAD result data are additionally written in the relevant data (FIG. 6).

As described above, according to the second embodiment, since the display and the CAD arithmetic operation are separately performed at different workstations 14 and 14a, a processing time for the CAD can be shortened. That is, if a CAD processing is performed at devices such as the modality 10, the workstation 14, and the data base 12, a long processing time is required for they share a single CPU. However, since the CAD processor 120 has a CPU 88 for a processing purpose only, the processing time is shortened.

A third embodiment is different from the first embodiment in that a CAD result is output as a sound. For this purpose, a workstation of this embodiment has a sound generator as shown in FIG. 37 in addition to the arrangement shown in FIG. 10. The CPU 88 of the workstation 14 reads out relevant data using the CRT image display control table (FIG. 14). The CPU 88 also reads out CAD results (FIG. 22) by reading out the CAD result address from the relevant data. When the CAD result is to be output, the CPU 88 starts a program in the ROM 92 and assigns the CAD result having abnormality to a corresponding output device in accordance with the pattern of the abnormality. In this program, the CAD results and the classification of the CAD result are read out from the semiconductor memory 86, and, if the type of abnormality indicates "diffuse", a text sentence generator is activated in order to output an abnormality alarm in the form of a text sentence. If the type of abnormality indicates "local", a marker generator and the sound generator shown in FIG. 37 are activated in order to indicate the position of the abnormality by means of a marker and a sound.

When the CAD operation result is read out from the semiconductor memory 86, if the pattern of abnormality indicates "local", a sound of "abnormality present" is simply generated. If, however, the pattern of abnormality indicates "diffuse", a statement formed as a text sentence is automatically read. The text sentence is, for example, "interstitial lung disease, upper right lung abnormal." The expression in the underlined portion changes in accordance with an abnormal portion. Next, the CPU 88 activates a program in the ROM 122 and converts character string data in the text sentence into a voice sound. "Interstitial lung disease, upper right lung abnormal" is stated by generating three groups of words, interstitial lung disease, upper right lung, and abnormal. Since the expression in the underlined portion changes in accordance with an abnormal portion as described above, a sound data base 124 is also provided to generate words for this purpose.

According to the third embodiment as described above, in specifying the position of abnormality by means of a sentence or a sound, words representing a position are used to make it easy to recognize the abnormality. Therefore, an oversight of a disease and consequently an erroneous diagnosis can be prevented to lead to an increase in diagnosis precision.

As a fourth embodiment, an embodiment of automatically outputting a CAD result will be explained. The arrangement of a workstation of the fourth embodiment is identical to that of the first embodiment shown in FIG. 12. In the fourth embodiment, however, even if no CAD result request is present during image reading of a conventional X-ray radiograph of chest, the result is automatically displayed.

For this purpose, each time an image is displayed, the CPU 88 refers to the CRT image display control table (FIG. 14) and checks whether the ID of the CAD result is included in the relevant data of the displayed image, i.e., whether nothing is stored in the CAD result ID, and in this manner checks whether the displayed image is an object of the CAD. If the CPU 88 determines that the displayed image is an object of the CAD, it measures a predetermined time from the start of image display by means of the timer 90, and automatically generates a trigger for requesting a CAD result output when the predetermined time has elapsed. This predetermined time can be arbitrarily changed In this manner, the output request for the CAD data can be omitted, and this results in a reduction in labors. In addition, if the CAD data is output immediately after an image is displayed, an operator or doctor may have a preconceived knowledge. Therefore, CAD data is output when a certain time has elapsed after an image is displayed. As a consequence, an erroneous diagnosis due to an oversight is prevented to improve diagnosis precision.

A fifth embodiment as another example of automatically outputting the CAD result will be described. Here, the arrangement of a workstation of this embodiment is also the same as that shown in FIG. 12. First, each time an image is displayed, the CPU 88 refers to the CRT image display control table (FIG. 14) and checks whether the ID of the CAD result is included in the relevant data of the displayed image, i.e., whether nothing is stored in the CAD result ID, and in this manner checks whether the displayed image is an object of the CAD. If the CPU 88 determines that the displayed image is an object of the CAD, it measures a number of times (the number of applications of the CAD algorithm) at which the image is displayed from the start of the image reading for the patient and writes the number of times into the relevant data (FIG. 6). The number of times is initially set to zero and increased by one every time the image is displayed. The CPU 88 automatically generates a trigger for requesting a CAD result output when the number of times reaches a predetermined time which can be arbitrarily set.

In this manner, since an output request for CAD data can be omitted, labors can be reduced. In addition, if CAD data is output immediately after an image is displayed, an operator or doctor may have a preoccupied knowledge. Therefore, CAD data is not output when an image is displayed for the first time and image reading is performed but output when the image is displayed for a predetermined time or the image display is switched. The result is that an erroneous diagnosis caused by an oversight is prevented to improve diagnosis precision.

The fourth and fifth embodiments are embodiments automatically outputting a CAD result. Next, a sixth embodiment of automatically ending outputting of a CAD result will be described. The arrangement of a workstation of this embodiment is identical to that shown in FIG. 12. When, for example, image reading of a conventional radiograph of a chest is performed, a display of the CAD result is automatically stopped even if no CAD result request is present. For this purpose, each time an image is displayed, the CPU 88 refers to the CRT image display control table (FIG. 14) and checks whether the ID of the CAD result is included in the relevant data of the displayed image, i.e., whether nothing is stored in the CAD result ID, and in this manner checks whether the displayed image is an object of the CAD. If the CPU 88 determines that the displayed image is an object of the CAD, it measures a predetermined time from the start of image display by means of the timer 90, and automatically generates a trigger for requesting the end of the CAD result output when the predetermined time has elapsed. This predetermined time can be arbitrarily changed. Upon the end of outputting, the CPU 88 turns off all overlay screens displayed on CRTs.

According to this embodiment, since an output end request for CAD data can be omitted, labors are reduced. In addition, CAD data remaining on an image for a long time makes it difficult for an operator or doctor to observe details of an image. As in this embodiment, however, by automatically ending display of CAD data after the data has been displayed for a predetermined time, an erroneous diagnosis is prevented to increase diagnosis precision.

Various commands must be input in the present invention, so a seventh embodiment relating to a modification of the input device will be described below. During image reading of a conventional radiograph of a chest, when an icon displayed on a CRT screen is designated (clicked) by a pointing device such as a mouse, a menu window as shown in FIG. 38A appears at a corner, in this case, the upper right corner of the screen. It is to be noted that this menu window shows only buttons which can be used by an operator at the time of click. If it is electrically sensed that a CAD button in the menu window on the screen is designated by the pointing device, a trigger for requesting a CAD result output is generated.

Similarly, when the icon displayed on the CRT screen is designated (clicked) by the pointing device such as a mouse, as shown in FIG. 38B, while the CAD output is performed, the menu window emerges. If a button for requesting a CAD detail result output in the menu window is designated, a trigger for requesting the CAD detail result output is generated. When the icon displayed on the CRT screen is designated (clicked) by the pointing device such as a mouse while the CAD output is performed, the menu window appears. If a button for requesting an option output in the menu window is designated, a trigger for requesting an option output is generated. When the icon displayed on the CRT screen is designated (clicked) by the pointing device such as a mouse while the CAD output is performed, the menu window emerges. If a button for requesting a CAD diagnosis level output in the menu window is designated, a trigger for requesting the CAD diagnosis level output is generated. When the icon displayed on the CRT screen is designated (clicked) by the pointing device such as a mouse while the CAD output is performed, the menu window appears. If a button for requesting a CAD result output end in the menu window is designated, a trigger for requesting the CAD detail output end is generated. Upon the end of outputting, overlay screens are turned off.

According to this embodiment as described above, a menu window including buttons having command names is displayed on the CRT screen. By designating a command with by means of a pointing device such as a mouse, a command for outputting CAD data can be input. In addition, since the menu window is not constantly displayed but can be selectively displayed, an operator (doctor) can display commands only when he or she needs them. Therefore, an annoyance caused by frequent changes in commands displayed can be reduced. In this case, a usable menu is prepared for each level (hierarchical level) of the contents of CAD data to be output. Therefore, since a user need only select a menu of interest from the prepared menus, a labor of selecting from a large number of menus is reduced.

An eighth embodiment concerned with coloring of a marker and a text sentence will be described below. The arrangement of a workstation is the same as that shown in FIG. 12. With reference to the CRT image display control table (FIG. 14), an overlay screen corresponding to a CRT not having "nothing" in the ID of the CAD result of relevant data of a displayed image is overlaid on the examination image displayed on the CRT. At this time, the data displayed on the overlay screen is flickered in an arbitrary color, such as red, while being synchronized by the timer 90. The period of flickering is 2 Hz.

According to the eighth embodiment, it is possible to strongly attract attention because of the color of the alarm display. As a result, an erroneous diagnosis caused by an oversight can be prevented to consequently increase diagnosis precision. This effect can be further enhanced by flickering the alarm display.

A ninth embodiment in which a CAD arithmetic operation is started by the modality, such as a film digitizer 18 (FIG. 4) will be described. The arrangement of a workstation is identical to that shown in FIG. 12. In this embodiment, when the film digitizer 18 digitizes all the image data for one patient and inputs the imaging direction, the CPU 88 reads out examination data and relevant data sequentially from the HD unit 106 into the semiconductor memory 86. In order to refer to the table (FIG. 15) of CAD algorithms and corresponding attribute data, the modality and the examination object are read out from the examination data (FIG. 2) and the imaging direction and the CAD result ID address are read out from the relevant data (FIG. 6). These readout items of data are stored in the semiconductor memory 86. These items of data are compared with the attribute data of the image stored in the table (FIG. 15) of the ROM 92. If these items coincide with those of a given CAD algorithm, this image is determined to be an image to which the given CAD algorithm can be applied, and the operation of the CAD is started.

Upon the start of the CAD operation, image data determined to be an object of the CAD is read out into the semiconductor memory 86. The CPU 88 executes a CAD operation program written in the ROM 92 and stores the result in the semiconductor memory 86. The CPU 88 transfers, as data flowing through the network 16, the image data, the relevant data, the CAD result, and the examination data (for each examination) to the data base 12 via the LAN I/F 94. As shown in FIG. 34, the data base 12 handles the CAD result data as a part of the relevant data.

When data is transferred to the workstation 14 during image reading, the transferred data is temporarily stored in the HD unit 106. However, the CAD result is read out from the HD unit 106 into the semiconductor memory 86 upon reception of a CAD output request as a trigger. In this case, the workstation 14 does not perform any operation associated with the CAD but simply displays the CAD result. Whenever an image is displayed on the image display device (workstation), the CAD result for the displayed image is stored in the semiconductor memory 86. Therefore, a time from generation of an output request to display the CAD result is shortened.

In a tenth embodiment, a timing at which an arithmetic operation of a CAD is started is when all the image data of one patient is transferred to the data base 12. At this time, the CPU 88 reads out examination data and relevant data sequentially from the HD unit 106 into the semiconductor memory 86. In order to refer to the table (FIG. 15) of CAD algorithms and corresponding attribute data, the modality and the examination object are read out from the examination data (FIG. 2) and the imaging direction and the CAD result ID address are read out from the relevant data (FIG. 6). These readout items of data are stored in the semiconductor memory 86. These items of data are compared with the attribute data of the image stored in the table (FIG. 15) of the ROM 92. If these items coincide with those of a given CAD algorithm, this image is determined to be an image to which the given CAD algorithm can be applied, and the operation of the CAD is started.

Upon the start of the CAD operation, image data determined to be an object of the CAD is read out into the semiconductor memory 86. The CPU 88 executes a CAD operation program written in the ROM 92 and stores the result in the semiconductor memory 86. The CPU 88 transfers, as data flowing through the network 16, the image data, the relevant data, the CAD result, and the examination data (for each examination) to the data base 12 via the LAN I/F 94. As shown in FIG. 34, the data base 12 handles the CAD result data as a part of the relevant data.

When data is transferred to the workstation 14 during image reading, the transferred data is temporarily stored in the HD unit 106. However, the CAD result is read out from the HD unit 106 into the semiconductor memory 86 upon reception of a CAD output request as a trigger. In this case, the workstation 14 does not perform any operation associated with the CAD but simply displays the CAD result. Whenever an image is displayed on the image display device (workstation), the CAD result for the displayed image is stored in the semiconductor memory 86. Therefore, a time from generation of an output request to display the CAD result is shortened.

FIG. 39 is a block diagram showing the arrangement of an eleventh embodiment. In the eleventh embodiment, a CAD processor 14a as shown in FIG. 36 is connected to the arrangement of the PACS shown in FIG. 1. When a request of starting a CAD operation is generated in the workstation 14, the CAD processor 14a is used to perform only the CAD operation at a high speed. Therefore, the workstation 14 transfers data required for the CAD operation to the CAD processor 14a, and only the result is returned to the workstation 14.

A timing at which the CAD operation is started is similar to that in the tenth embodiment. However, unlike in the tenth embodiment, the CAD operation is performed by the CAD processor 14a. The workstation 14 supplies the image data, the examination data, and the relevant data to the CAD processor 14a via the network 16. As shown in FIG. 36, the CAD processor 14a has its own CPU, and by means of the CPU it executes the CAD operation and outputs the CAD result. The result of the CAD operation is transferred as result data having the format shown in FIG. 22 to the workstation 14 via the network 16. As shown in FIG. 34, the workstation 14 or the data base 12 handles the CAD result as a part of the relevant data.

When data is transferred to the workstation 14 during image reading, the transferred data is temporarily stored in the HD unit 106. The CAD result, however, is read out from the HD unit 106 into the semiconductor memory 86 upon reception of an output request for the CAD as a trigger. In this case, the workstation 14 does not perform any operation associated with the CAD but simply displays the result.

Processing executed by devices such as the modality, the workstation, and the data base takes a long processing time for they share a CPU. In this embodiment, however, since the processor having a CPU for a processing purpose only executes the processing, a processing time can be shortened.

Figure 42A:
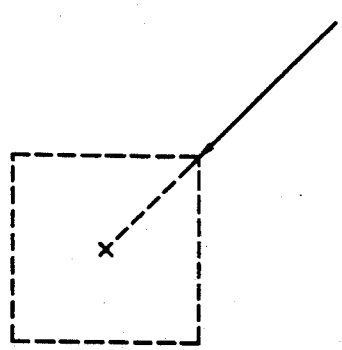
FIGS. 42A and 42B show still another modifications of the marker display according to the twelfth embodiment.
Figure 42B:
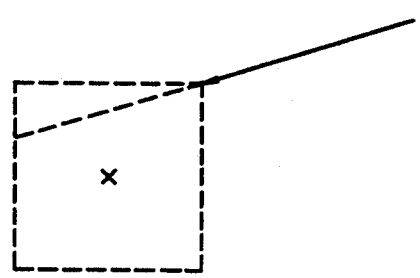

As a twelfth embodiment, an embodiment concerned with a modification of a marker will be described below. FIGS. 40A to 40E show modifications of a marker for pointing the ROI, and FIGS. 41A to 41F show modifications of a marker for surrounding the ROI. Pointing the ROI includes a case in which the direction of an arrow points the center of the ROI as shown in FIG. 42A and a case in which it points a position other than the center as shown in FIG. 42B.

According to this embodiment, an alarming means which strongly attracts attention is used in order to alarm abnormality. Therefore, an oversight and therefore an erroneous diagnosis can be prevented, and this results in an improvement in diagnosis precision.

A thirteenth embodiment in which an on/off of the CAD result display is controlled for each of the CRTs will be described. The touch panel includes plural CAD result display buttons provided for the respective CRTs. In order to display only the CAD result on the CRT #1, it is necessary to depress the CAD result display buttons for the CRT #1. When the depression of that button is detected, the ID of the image displayed on the CRT #1 is read out from the CRT display control table (FIG. 14). The CAD result address is read out from the relevant data of the image and the CAD result data is written into the overlay memory for the CRT #1, thereby displaying the CAD result overlapped on the image. As described above, the operation of this embodiment is the same as that of the first embodiment except that the image ID is read out from the CRT display control table. If no CAD result address is stored (nothing is stored in the CAD result ID), the same operation as the first embodiment is performed from application of a suitable CAD algorithm to the image data to writing the CAD result address into the table.

According to the thirteenth embodiment, only necessary CAD results are selectively displayed during the reading of the images displayed on the CRTs of the workstation, therefore, the display is not complicated due to the omission of display of unnecessary CAD result.

A fourteenth embodiment which is a modification of the thirteenth embodiment will be descried. In this embodiment, when the image ID of the CRT display control table is updated upon changing the image to be displayed, the CAD result address is read out from the relevant data of the new image and the CAD result is written into the overlay memory, thereby displaying the CAD result overlapped on the image. That is, when the image ID is designated, the CAD result is automatically displayed regardless of whether or not the image has been read. If no CAD result address is stored (nothing is stored in the CAD result ID), the same operation as the first embodiment is performed from application of a suitable CAD algorithm to the image data to writing the CAD result address into the table. When the depression of the CAD display button for a reference image (an image other than the image which has been read), the IDs of the images displayed on the CRTs are read out from the CRT display control table (FIG. 14) and it is determined whether or not the image has been read. If the image has been read, the CAD result address is read out from the relevant data and the CAD result is written into the overlay memory, thereby displaying the CAD result overlapped on the image. For all the CRTs, this operation is performed. It is to be noted that all the data in the overlay memory are deleted before the CAD result is written into the memory.

According to the fourteenth embodiment, since the CAD result is automatically output upon changing the image to be displayed, labors for instructing the CAD result output. It is possible to make a comparison diagnosis with reference to the reference image which has been read, thereby improving the diagnosis precision.

A fifteenth embodiment as a modification of the thirteenth embodiment will be described. The touch panel includes a single CAD result display button provided for all the CRTs. When the depression of the display button is detected, the IDs of the images displayed on the CRTs are read out from the CRT display control table (FIG. 14). The CAD result addresses for all the images are read out from the relevant data and the CAD result data are written into the overlay memories for all the CRTs, thereby displaying the CAD results overlapped on the images. The CAD results are automatically displayed regardless of whether or not the images have been read. If no CAD result address is stored (nothing is stored in the CAD result ID), the same operation as the first embodiment is performed from application of a suitable CAD algorithm to the image data to writing the CAD result address into the table.

According to the fifteenth embodiment, since it is possible to make a comparison diagnosis with reference to the reference image which has been read, thereby improving the diagnosis precision. When the CAD result display is desired, it is sufficient to touch only one button so that the operation is simple.

A sixteenth embodiment which is a further modification of the thirteenth embodiment will be described. The touch panel includes a CAD result display button for the image which has not been read and a CAD result display button for the reference image (an image other than the image which has not been read). When the depression of the CAD result display button for the image which has not been read is detected, the IDs of the images displayed on the CRTs are read out from the CRT display control table (FIG. 14). It is determined whether or not the image has not been read based on the relevant data of the image. If the image is detected as being not read, the CAD result address is read out from the relevant data of the image and the CAD result data is written into the overlay memory. All the data in the overlay memory are deleted before the CAD result is written into the memory. When the depression of the CAD result display button for the reference image is detected, the IDs of the images displayed on the CRTs are read out from the CRT display control table (FIG. 14). It is determined whether or not the image has not been read based on the relevant data of the image. If the image is detected as being not read, the CAD result address is read out from the relevant data of the image and the CAD result data is written into the overlay memory. All the data in the overlay memory are deleted before the CAD result is written into the memory. If no CAD result address is stored (nothing is stored in the CAD result ID), the same operation as the first embodiment is performed from application of a suitable CAD algorithm to the image data to writing the CAD result address into the table.

According to the sixteenth embodiment, since it is possible to make a comparison diagnosis with reference to the reference image which has been read, thereby improving the diagnosis precision. When the CAD result display is desired, it is sufficient to touch only one button so that the operation is simple.

A seventeenth embodiment will be described. Though the above description, a suitable CAD algorithm is selected by the computer using the attribute data, in this embodiment, the doctor designates the name of the CAD algorithm. Before reading of the image, the doctor selects one or more CAD algorithms as well as inputting the examination ID. The names of the selected algorithms are arranged in the form of the table as shown in FIG. 43. When the image is input to the workstation, the CAD algorithms in the table are sequentially applied to the images. The other operation is the same as the first embodiment.

According to the seventeenth embodiment, only a desired CAD result is selectively displayed and the display becomes simple.

Additional advantages and modifications will be readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

As has been described above, according to the present invention, there is provided a computer-aided diagnosis system for medical use, which outputs computer-aided diagnosis data with a high precision by a simple operation having no adverse effect on diagnosis made by doctors and a picture archiving communication system incorporating the computer-aided diagnosis system for medical use and having a high diagnosis precision.

What is claimed is:

1. A system for automatically analyzing a medical image using a predetermined computer-aided diagnosis algorithm, comprising:
    means for inputting a single medical image of a plurality of medical images of different types and attributes data of the medical image, said attribute data denoting the type of the medical image;
    means for determining, based on the attribute data, whether or not the predetermined computer-aided diagnosis algorithm can be applied to the medical image by a comparison of the input attribute data with the predetermined computer-aided diagnosis algorithm;
    means for analyzing the medical image using the predetermined computer-aided diagnosis algorithm in accordance with a result of a determination of said determining means indicates that the predetermined computer-aided diagnosis algorithm can be applied to the medical image; and
    means for displaying an analysis result of said analyzing means.

2. A system according to claim 1, which further comprises:
    modalities for providing the medical image, said modalities including at least said input means; and
    a network for connecting said modalities with said analyzing means, said determining means, and said display means.

3. A system for automatically analyzing a medical image, comprising:
    means for inputting a medical image of a plurality of medical images of different types and attribute data of the medical image, said attribute data denoting the type of the medical image;

means for storing a plurality of computer-aided diagnosis algorithms which correspond respectively to a plurality of types of the medical images;

means for selecting, based on the attribute data, an optimum computer-aided diagnosis algorithm suitable for the medical image input by said inputting means;

means for analyzing the medical image using the optimum computer-aided diagnosis algorithm selected by said selecting means; and means for displaying an analysis result of said analyzing means.

4. A system according to claim 3, which further comprises:

modalities for providing the medical images, said modalities including at least said input means; and a network for connecting said modalities with said analyzing means, said determining means, and said display means.

5. A system for automatically analyzing a medical image, comprising:

means for storing a plurality of medical images of different types and attribute data of the medical images, said attribute data denoting the type of the medical image;

means for storing a plurality of computer-aided diagnosis algorithms which correspond respectively to a plurality of types of the medical images;

means for selecting, based on the attribute data, optimum computer-aided diagnosis algorithms suitable for diagnosis of the medical images stored in said image and attribute data storing means;

means for analyzing the medical images using computer-aided diagnosis algorithms which are selected by said selecting means;

means for storing an analysis result of said analyzing means in association with the medical images, as the attribute data of the image; and means for selectively reading out a desired medical image and a corresponding analysis result and displaying the desired medical image and the corresponding analysis result.

6. A system according to claim 5, which further comprises:

modalities for providing the medical image, said modalities including at least said input means; and a network for connecting said modalities with said analyzing means, said determining means, and said display means.

7. A system according to claim 5, wherein said reading and displaying means comprises:

means for inputting retrieval data; and means for reading out an analysis result which is in accordance with the retrieval data.

8. A system for automatically analyzing a medical image, comprising:

means for storing a plurality of medical images and attribute data of the medical images, said attribute data denoting whether or not the medical image has been viewed by an operator;

means for selectively extracting one of first medical images which have been viewed by an operator and second medical images which have not been viewed by an operator based on the attribute data;

means for analyzing one of the first medical images and the second medical images extracted by said extracting means using a computer-aided diagnosis algorithm; and means for displaying an analysis result of said analyzing means.

9. A system according to claim 8, wherein said storing means further stores the analysis result in association with the medical images.

10. A system according to claim 8, wherein said storing means stores an item of the attribute data denoting whether or not the medical image has been analyzed by said analyzing means.

11. A system according to claim 10, wherein said extracting means extracts medical images which have been viewed but have not been analyzed by said analyzing means.

12. A system for automatically analyzing a medical image using a computer-aided diagnosis algorithm, comprising:

means for storing a plurality of medical images and attribute data of the medical images, the attribute data including an item of data denoting whether or not the medical image has been analyzed using a computer-aided diagnosis algorithm, an item of data denoting whether or not the medical image has been viewed by an operator, and an item of data denoting a type of the medical image;

means for storing a plurality of computer-aided diagnosis algorithms;

means for analyzing medical images which are stored in said storing means, have not been analyzed using a computer-aided diagnosis algorithm, and have been viewed by an operator using an optimum computer-aided diagnosis algorithm selected based on the attribute data;

means for storing an analysis result of said analyzing means in association with the medical images; and means for selectively reading out a desired medical image and a corresponding analysis result and displaying the desired medical image and the corresponding analysis result.

13. A system according to claim 1, wherein said analyzing means comprises means for determining a position, a type, and a degree of abnormality, and said displaying means comprises means for displaying the position of abnormality and means for displaying a text representing the type and the degree of abnormality.

14. A system according to claim 13, wherein said analyzing means comprises means for hierarchically determining the position, the type, and the degree of abnormality, and said displaying means comprises means for displaying the position of abnormality, and means for stopping display of the position of abnormality as well as for displaying the text representing the type and the degree of the abnormality when a display command is input while the position of abnormality is displayed.

15. A system according to claim 1, wherein said displaying means comprises means for flickering display of the result of said analyzing means.

16. A system according to claim 1, which further comprises means for sounding the analysis result of said analyzing means.

17. A system according to claim 1, wherein said displaying means comprises means for displaying the medical image and means for starting display of the analysis result after a predetermined period of time has elapsed from start of display of the medical image.

18. A system according to claim 1, wherein said displaying means comprises means for displaying the medical image, means for counting the number of times a medical image has been displayed, and means for starting display of the analysis result if the medical image is displayed at predetermined times.

19. A system according to claim 1, which further comprises means for stopping display of the analysis result after a predetermined period of time has elapsed from start of the display of the analysis result.

20. A system according to claim 1, wherein said attribute data denotes an imaging source of the medical image, an object to be diagnosed, and an imaging direction of the medical image.

21. A system according to claim 1, wherein said determining means comprises means for storing reference attribute data which corresponds to the predetermined computer-aided diagnosis algorithm and means for comparing the attribute data of the medical image and the reference attribute data, thereby determining that the medical image is adapted to the predetermined computer-aided diagnosis algorithm when the attribute data of the medical image coincides with the reference attribute data.

22. A system according to claim 3, wherein said analyzing means comprises means for determining a position, a type, and a degree of abnormality, and said displaying means comprises means for displaying the position of abnormality and means for displaying a text representing the type and the degree of abnormality.

23. A system according to claim 22, wherein said analyzing means comprises means for hierarchically determining the position, the type, and the degree of abnormality, and said displaying means comprises means for displaying the position of abnormality, and means for stopping display of the position of abnormality as well as for displaying the text representing the type and the degree of the abnormality when a display command is input while the position of abnormality is displayed.

24. A system according to claim 3, wherein said displaying means comprises means for flickering display of the result of said analyzing means.

25. A system according to claim 3, which further comprises means for sounding the analysis result of said analyzing means.

26. A system according to claim 3, wherein said displaying means comprises means for displaying the medical image and means for starting display of the analysis result after a predetermined period of time has elapsed from start of display of the medical image.

27. A system according to claim 3, wherein said displaying means comprises means for displaying the medical image, means for counting the number of times a medical image has been displayed, and means for starting display of the analysis result if the medical image is displayed at predetermined times.

28. A system according to claim 3, which further comprises means for stopping display of the analysis result after a predetermined period of time has elapsed from start of the display of the analysis result.

29. A system according to claim 3, wherein said attribute data denotes an imaging source of the medical image, an object to be diagnosed, and an imaging direction of the medical image.

30. A system according to claim 3, wherein said determining means comprises means for storing reference attribute data which corresponds to the predetermined computer-aided diagnosis algorithm and means for comparing the attribute data of the medical image and the reference attribute data, thereby determining that the medical image is adapted to the predetermined computer-aided diagnosis algorithm when the attribute data of the medical image coincides with the reference attribute data.

31. A system according to claim 5, wherein said analyzing means comprises means for determining a position, a type, and a degree of abnormality, and said displaying means comprises means for displaying the position of abnormality and means for displaying a text representing the type and the degree of abnormality.

32. A system according to claim 31, wherein said analyzing means comprises means for hierarchically determining the position, the type, and the degree of abnormality, and said displaying means comprise means for displaying the position of abnormality, and means for stopping display of the position of abnormality as well as for displaying the text representing the type and the degree of the abnormality when a display command is input while the position of abnormality is displayed.

33. A system according to claim 5, wherein said displaying means comprises means for flickering display of the result of siad analyzing means.

34. A system according to claim 5, which further comprises means for sounding the analysis result of said analyzing means.

35. A system according to claim 5, wherein said displaying means comprises means for displaying the medical image and means for starting display of the analysis result after a predetermined period of time has elapsed from start of display of the medical image.

36. A system according to claim 5, wherein said displaying means comprises means for displaying the medical image, means for counting the number of times a medical image has been displayed, and means for starting display of the analysis result if the medical image is displayed at predetermined times.

37. A system according to claim 5, which further comprises means for stopping display of the analysis result after a predetermined period of time has elapsed from start of the display of the analysis result.

38. A system according to claim 5, wherein said attribute data denotes an imaging source of the medical image, an object to be diagnosed, and an imaging direction of the medical image.

39. A system according to claim 5, wherein said determining means comprises means for storing reference attribute data which corresponds to the predetermined computer-aided diagnosis algorithm and means for comparing the attribute data of the medical image and the reference attribute data, thereby determining that the medical image is adapted to the predetermined computer-aided diagnosis algorithm when the attribute data of the medical image coincides with the reference attribute data.

40. A system according to claim 8, wherein said analyzing means comprises means for determining a position, a type, and a degree of abnormality, and said displaying means comprises means for displaying the position of abnormality and means for displaying a text representing the type and the degree of abnormality.

41. A system according to claim 40, wherein said analyzing means comprises means for hierarchically determining the position, the type, and the degree of abnormality, and said displaying means comprises means for displaying the position of abnormality, and means for stopping display of the position of abnormality as well as for displaying the text representing the type and the degree of the abnormality when a display command is input while the position of abnormality is displayed.

42. A system according to claim 8, wherein said displaying means comprises means for flickering display of the result of said analyzing means.

43. A system according to claim 8, which further comprises means for sounding the analysis result of said analyzing means.

44. A system according to claim 8, wherein said displaying means comprises means for displaying the medical image and means for starting display of the analysis result after a predetermined period of time has elapsed from start of display of the medical image.

45. A system according to claim 8, wherein said displaying means comprises means for displaying the medical image, means for counting the number of times a medical image has been displayed, and means for starting display of the analysis result if the medical image is displayed at predetermined times.

46. A system according to claim 8, which further comprises means for stopping display of the analysis result after a predetermined period of time has elapsed from start of the display of the analysis result.

47. A system according to claim 8, wherein said attribute data denotes an imaging source of the medical image, an object to be diagnosed, and an imaging direction of the medical image.

48. A system according to claim 8, wherein said determining means comprises means for storing reference attribute data which corresponds to the predetermined computer-aided diagnosis algorithm and means for comparing the attribute data of the medical image and the reference attribute data, thereby determining that the medical image is adapted to the predetermined computer-aided diagnosis algorithm when the attribute data of the medical image coincides with the reference attribute data.

49. A system according to claim 12, wherein said analyzing means comprises means for determining a position, a type, and a degree of abnormality, and said displaying means comprises means for displaying the position of abnormality and means for displaying a text representing the type and the degree of abnormality.

50. A system of claim 49, wherein said analyzing means comprises means for hierarchically determining the position, the type, and the degree of abnormality, and said displaying means comprises means for displaying the position of abnormality, and means for stopping display of the position of abnormality as well as for displaying the text representing the type and the degree of the abnormality when a display command is input while the position of abnormality is displayed.

51. A system according to claim 12, wherein said displaying means comprises means for flickering display of the result of said analyzing means.

52. A system according to claim 12, which further comprises means for sounding the analysis result of said analyzing means.

53. A system according to claim 12, wherein said displaying means comprises means for displaying the medical image and means for starting display of the analysis result after a predetermined period of time has elapsed from start of display of the medical image.

54. A system according to claim 12, wherein said displaying means comprises means for displaying the medical image, means for counting the number of times a medical image has been displayed, and means for starting display of the analysis result if the medical image is displayed at predetermined times.

55. A system according to claim 12, which further comprises means for stopping display of the analysis result after a predetermined period of time has elapsed from start of the display of the analysis result.

56. A system according to claim 12, wherein said attribute data denotes an imaging source of the medical image, an object to be diagnosed, and an imaging direction of the medical image.

57. A system according to claim 12, wherein said determining means comprises means for storing reference attribute data which corresponds to the predetermined computer-aided diagnosis algorithm and means for comparing the attribute data of the medical image and the reference attribute data, thereby determining that the medical image is adapted to the predetermined computer-aided diagnosis algorithm when the attribute data of the medical image coincides with the reference attribute data.

* * * * *